US007910641B2

(12) United States Patent
Myers

(10) Patent No.: US 7,910,641 B2
(45) Date of Patent: Mar. 22, 2011

(54) PH MODULATED FILMS FOR DELIVERY OF ACTIVES

(75) Inventor: Garry L. Myers, Kingsport, TN (US)

(73) Assignee: Monosol Rx, LLC, Portage, IN (US)

(*) Notice: Subject to any disclaimer, the term of this patent is extended or adjusted under 35 U.S.C. 154(b) by 982 days.

(21) Appl. No.: 11/639,013

(22) Filed: Dec. 14, 2006

(65) Prior Publication Data

US 2007/0149731 A1 Jun. 28, 2007

Related U.S. Application Data

(63) Continuation-in-part of application No. 10/074,272, filed on Feb. 14, 2002, now Pat. No. 7,425,292.

(60) Provisional application No. 60/754,092, filed on Dec. 27, 2005, provisional application No. 60/328,868, filed on Oct. 12, 2001, provisional application No. 60/386,937, filed on Jun. 7, 2002.

(51) Int. Cl.
C08L 5/04 (2006.01)
C08L 71/02 (2006.01)
C09D 105/04 (2006.01)
C09D 171/02 (2006.01)
A61F 13/00 (2006.01)
A61K 9/70 (2006.01)
A61L 15/12 (2006.01)

(52) U.S. Cl. .......... 524/28; 106/162.8; 106/205.01; 106/205.71; 424/443; 424/447

(58) Field of Classification Search .......... 524/28; 106/205.71, 162.8, 205.01; 424/447, 443; 604/358
See application file for complete search history.

(56) References Cited

U.S. PATENT DOCUMENTS

| | | | |
|---|---|---|---|
| 307,537 A | 11/1884 | Foulks |
| 688,446 A | 12/1901 | Stempel |
| 2,142,537 A | 1/1939 | Tisza |
| 2,277,038 A | 3/1942 | Curtis |
| 2,352,691 A | 7/1944 | Curtis |
| 2,501,544 A | 3/1950 | Shrontz |
| 2,980,554 A | 4/1961 | Gentile et al. |
| 3,249,109 A | 5/1966 | Maeth et al. |
| 3,444,858 A | 5/1969 | Russell |
| 3,536,809 A | 10/1970 | Applezweig |
| 3,551,556 A | 12/1970 | Kliment et al. |
| 3,598,122 A | 8/1971 | Zaffaroni |
| 3,632,740 A | 1/1972 | Robinson et al. |
| 3,640,741 A | 2/1972 | Etes |
| 3,641,237 A | 2/1972 | Gould et al. |
| 3,731,683 A | 5/1973 | Zaffaroni |
| 3,753,732 A | 8/1973 | Boroshok |
| 3,814,095 A | 6/1974 | Lubens |
| 3,892,905 A | 7/1975 | Albert |
| 3,911,099 A | 10/1975 | DeFoney et al. |
| 3,972,995 A | 8/1976 | Tsuk et al. |
| 3,996,934 A | 12/1976 | Zaffaroni |
| 3,998,215 A | 12/1976 | Anderson et al. |
| 4,029,757 A | 6/1977 | Mlodozeniec et al. |
| 4,029,758 A | 6/1977 | Mlodozeniec et al. |
| 4,031,200 A | 6/1977 | Reif |
| 4,123,592 A | 10/1978 | Rainer et al. |
| 4,128,445 A | 12/1978 | Sturzenegger et al. |
| 4,136,145 A | 1/1979 | Fuchs et al. |
| 4,136,162 A | 1/1979 | Fuchs et al. |
| 4,139,627 A | 2/1979 | Lane et al. |
| 4,226,848 A | 10/1980 | Nagai et al. |
| 4,251,400 A | 2/1981 | Columbus |
| 4,292,299 A | 9/1981 | Suzuki et al. |
| 4,294,820 A | 10/1981 | Keith et al. |
| 4,302,465 A | 11/1981 | Ekenstam et al. |
| 4,307,075 A | 12/1981 | Martin |
| 4,325,855 A | 4/1982 | Dickmann |
| 4,373,036 A | 2/1983 | Chang et al. |
| 4,406,708 A | 9/1983 | Hesselgren |
| 4,432,975 A | 2/1984 | Libby |
| 4,438,258 A | 3/1984 | Graham |
| 4,460,562 A | 7/1984 | Keith et al. |
| 4,466,973 A | 8/1984 | Rennie |
| 4,503,070 A | 3/1985 | Eby |
| 4,515,162 A | 5/1985 | Yamamoto |
| 4,517,173 A | 5/1985 | Kizawa et al. |
| 4,529,601 A | 7/1985 | Broberg et al. |

(Continued)

FOREIGN PATENT DOCUMENTS

| | | |
|---|---|---|
| DE | 2432925 B2 | 1/1976 |
| DE | 2449865 B2 | 4/1976 |
| DE | 3630603 C2 | 3/1988 |
| EP | 0241178 A1 | 10/1987 |
| EP | 0285568 A2 | 10/1988 |
| EP | 0219762 B1 | 12/1990 |
| EP | 0259749 B1 | 8/1991 |
| EP | 200508 | 10/1991 |
| EP | 273069 | 10/1992 |
| EP | 0514691 | 11/1992 |
| EP | 0250187 B1 | 9/1993 |
| EP | 0452446 B1 | 12/1993 |
| EP | 381194 | 8/1994 |

(Continued)

OTHER PUBLICATIONS

Barton, "Citric Buffer Calculations" http://www.egr.msu.edu/scb-group/tools/citric/cit.htm (Nov. 2000).*
Lazaridou et al.; Thermophysical properties of chitosan, chitosan-starch and chitosan-pullulan films near the glass transition; Elsevier Science Ltd.; 2002; pp. 179-190.
Office Action Chinese Application No. 200680049019.2, dated Apr. 30, 2010.

Primary Examiner — David M Brunsman
(74) Attorney, Agent, or Firm — Hoffmann & Baron, LLP

(57) ABSTRACT

The invention relates to pH modulated films and methods of their preparation. The film compositions include at least one component having a non-neutral pH when combined with water; and a pH modulated polymer system selected to reduce or prevent synerisis when combined with the non-neutral component in combination with aqueous media. The films demonstrate a non-self-aggregating uniform heterogeneity. Desirably, the films disintegrate in water and may be formed by a controlled drying process, extrusion process, or other process that maintains the required uniformity of the film.

42 Claims, 6 Drawing Sheets

U.S. PATENT DOCUMENTS

| | | |
|---|---|---|
| 4,529,748 A | 7/1985 | Wienecke |
| 4,562,020 A | 12/1985 | Hijiya et al. |
| 4,569,837 A | 2/1986 | Suzuki et al. |
| 4,593,053 A | 6/1986 | Jevne |
| 4,608,249 A | 8/1986 | Otsuka et al. |
| 4,615,697 A | 10/1986 | Robinson |
| 4,623,394 A | 11/1986 | Nakamura et al. |
| 4,652,060 A | 3/1987 | Miyake |
| 4,659,714 A | 4/1987 | Watt-Smith |
| 4,675,009 A | 6/1987 | Hymes et al. |
| 4,695,465 A | 9/1987 | Kigasawa et al. |
| 4,704,119 A | 11/1987 | Shaw et al. |
| 4,713,239 A | 12/1987 | Babaian et al. |
| 4,713,243 A | 12/1987 | Schiraldi et al. |
| 4,722,761 A | 2/1988 | Cartmell et al. |
| 4,740,365 A | 4/1988 | Yukimatsu et al. |
| 4,748,022 A | 5/1988 | Busciglio |
| 4,765,983 A | 8/1988 | Takayanagi et al. |
| 4,772,470 A | 9/1988 | Inoue et al. |
| 4,777,046 A | 10/1988 | Iwakura et al. |
| 4,789,667 A | 12/1988 | Makino et al. |
| 4,849,246 A | 7/1989 | Schmidt |
| 4,860,754 A | 8/1989 | Sharik et al. |
| RE33,093 E | 10/1989 | Schiraldi et al. |
| 4,876,092 A | 10/1989 | Mizobuchi et al. |
| 4,876,970 A | 10/1989 | Bolduc |
| 4,888,354 A | 12/1989 | Chang et al. |
| 4,894,232 A | 1/1990 | Reul et al. |
| 4,900,552 A | 2/1990 | Sanvordeker et al. |
| 4,900,554 A | 2/1990 | Yanagibashi et al. |
| 4,900,556 A | 2/1990 | Wheatley et al. |
| 4,910,247 A | 3/1990 | Haldar et al. |
| 4,915,950 A | 4/1990 | Miranda et al. |
| 4,925,670 A | 5/1990 | Schmidt |
| 4,927,634 A | 5/1990 | Sorrentino et al. |
| 4,927,636 A | 5/1990 | Hijiya et al. |
| 4,937,078 A | 6/1990 | Mezei et al. |
| 4,940,587 A | 7/1990 | Jenkins et al. |
| 4,948,580 A | 8/1990 | Browning |
| 4,958,580 A | 9/1990 | Asaba et al. |
| 4,978,531 A | 12/1990 | Yamazaki |
| 4,981,693 A | 1/1991 | Higashi et al. |
| 4,981,875 A | 1/1991 | Leusner et al. |
| 5,023,082 A | 6/1991 | Friedman et al. |
| 5,024,701 A | 6/1991 | Desmarais |
| 5,028,632 A | 7/1991 | Fuisz |
| 5,047,244 A | 9/1991 | Sanvordeker et al. |
| 5,064,717 A | 11/1991 | Suzuki et al. |
| 5,089,307 A | 2/1992 | Ninomiya et al. |
| 5,158,825 A | 10/1992 | Aitwirth |
| 5,166,233 A | 11/1992 | Kuroya |
| 5,186,938 A | 2/1993 | Sablotsky et al. |
| 5,229,164 A | 7/1993 | Pins et al. |
| 5,234,957 A | 8/1993 | Mantelle |
| 5,271,940 A | 12/1993 | Cleary et al. |
| 5,272,191 A | 12/1993 | Ibrahim et al. |
| 5,346,701 A | 9/1994 | Heiber et al. |
| 5,393,528 A | 2/1995 | Staab |
| 5,411,945 A | 5/1995 | Ozaki et al. |
| 5,413,792 A | 5/1995 | Ninomiya et al. |
| 5,433,960 A | 7/1995 | Meyers |
| 5,455,043 A | 10/1995 | Fischel-Ghodsian |
| 5,462,749 A | 10/1995 | Rencher |
| 5,472,704 A | 12/1995 | Santus |
| 5,518,902 A | 5/1996 | Ozaki et al. |
| 5,550,178 A * | 8/1996 | Desai et al. .................... 524/56 |
| 5,567,431 A | 10/1996 | Vert et al. |
| 5,620,757 A | 4/1997 | Ninomiya et al. |
| 5,629,003 A | 5/1997 | Horstmann et al. |
| 5,700,478 A | 12/1997 | Biegajski et al. |
| 5,700,479 A | 12/1997 | Lundgren |
| 5,766,620 A | 6/1998 | Herber et al. |
| 5,847,023 A * | 12/1998 | Viegas et al. ................. 523/106 |
| 5,948,430 A | 9/1999 | Zerbe et al. |
| 6,153,210 A | 11/2000 | Roberts et al. |
| 6,177,096 B1 | 1/2001 | Zerbe et al. |
| 6,231,957 B1 | 5/2001 | Zerbe et al. |
| 6,284,264 B1 | 9/2001 | Zerbe et al. |
| 2001/0006677 A1 | 7/2001 | McGinity et al. |
| 2001/0022964 A1 | 9/2001 | Leung et al. |
| 2001/0046511 A1 | 11/2001 | Zerbe et al. |
| 2003/0068378 A1 | 4/2003 | Chen et al. |
| 2005/0095272 A1* | 5/2005 | Augello ...................... 424/439 |

FOREIGN PATENT DOCUMENTS

| | | |
|---|---|---|
| EP | 1110546 | 6/2001 |
| FR | 2126270 | 10/1972 |
| WO | WO 91/05540 A1 | 5/1991 |
| WO | WO 92/15289 A1 | 9/1992 |
| WO | WO 95/05416 A2 | 2/1995 |
| WO | WO 95/18046 A1 | 7/1995 |
| WO | WO 00/18365 | 4/2000 |
| WO | WO 00/42992 | 7/2000 |
| WO | WO 01/70194 | 9/2001 |
| WO | WO 01/91721 | 12/2001 |

* cited by examiner

PH MODULATED FILMS FOR DELIVERY OF ACTIVES

CROSS-REFERENCE TO RELATED APPLICATIONS

This application claims priority to U.S. Provisional Application No. 60/754,092, filed Dec. 27, 2005, and is a continuation-in-part of U.S. application Ser. No. 10/074,272, filed Feb. 14, 2002, now U.S. Pat. No. 7,425,292 which claims priority to U.S. Provisional Application No. 60/328,868, filed Oct. 12, 2001, and U.S. Provisional Application No. 60/386,937, filed Jun. 7, 2002.

FIELD OF THE INVENTION

The invention relates to rapidly dissolving, self-supporting films and methods of their preparation. In particular, the films include a component having a non-neutral pH; and a pH modulated polymer system selected to reduce or prevent synerisis in the film.

BACKGROUND OF THE RELATED TECHNOLOGY

Films may be used as a delivery system to carry active ingredients such as drugs, pharmaceuticals, and the like. However, historically films and the process of making drug delivery systems therefrom have suffered from a number of unfavorable characteristics that have not allowed them to be used in practice.

Films that incorporate a pharmaceutically active ingredient are disclosed in expired U.S. Pat. No. 4,136,145 to Fuchs, et al. ("Fuchs"). These films may be formed into a sheet, dried and then cut into individual doses. The Fuchs disclosure alleges the fabrication of a uniform film, which includes the combination of water soluble polymers, surfactants, flavors, sweeteners, plasticizers and drugs. These allegedly flexible films are disclosed as being useful for oral, topical or enteral use. Examples of specific uses disclosed by Fuchs include application of the films to mucosal membrane areas of the body, including the mouth, rectal, vaginal, nasal and ear areas.

Examination of films made in accordance with the process disclosed in Fuchs, however, reveals that such films suffer from the aggregation or conglomeration of particles, i.e., self-aggregation, making them inherently non-uniform. This result can be attributed to Fuchs' process parameters, which although not disclosed likely include the use of relatively long drying times, thereby facilitating intermolecular attractive forces, convection forces, air flow and the like to form such agglomeration.

The formation of agglomerates randomly distributes the film components and any active present as well. When large dosages are involved, a small change in the dimensions of the film would lead to a large difference in the amount of active per film. If such films were to include low dosages of active, it is possible that portions of the film may be substantially devoid of any active. Since sheets of film are usually cut into unit doses, certain doses may therefore be devoid of or contain an insufficient amount of active for the recommended treatment. Failure to achieve a high degree of accuracy with respect to the amount of active ingredient in the cut film can be harmful to the patient. For this reason, dosage forms formed by processes such as Fuchs, would not likely meet the stringent standards of governmental or regulatory agencies, such as the U.S. Federal Drug Administration ("FDA"), relating to the variation of active in dosage forms. Currently, as required by various world regulatory authorities, dosage forms may not vary more than 10% in the amount of active present. When applied to dosage units based on films, this virtually mandates that uniformity in the film be present.

The problems of self-aggregation leading to non-uniformity of a film were addressed in U.S. Pat. No. 4,849,246 to Schmidt ("Schmidt"). Schmidt specifically pointed out that the methods disclosed by Fuchs did not provide a uniform film and recognized that that the creation of a non-uniform film necessarily prevents accurate dosing, which as discussed above is especially important in the pharmaceutical area. Schmidt abandoned the idea that a mono-layer film, such as described by Fuchs, may provide an accurate dosage form and instead attempted to solve this problem by forming a multi-layered film. Moreover, his process is a multi-step process that adds expense and complexity and is not practical for commercial use.

Other U.S. patents directly addressed the problems of particle self-aggregation and non-uniformity inherent in conventional film forming techniques. In one attempt to overcome non-uniformity, U.S. Pat. No. 5,629,003 to Horstmann et al. and U.S. Pat. No. 5,948,430 to Zerbe et al. incorporated additional ingredients, i.e. gel formers and polyhydric alcohols respectively, to increase the viscosity of the film prior to drying in an effort to reduce aggregation of the components in the film. These methods have the disadvantage of requiring additional components, which translates to additional cost and manufacturing steps. Furthermore, both methods employ the use the conventional time-consuming drying methods such as a high-temperature air-bath using a drying oven, drying tunnel, vacuum drier, or other such drying equipment. The long length of drying time aids in promoting the aggregation of the active and other adjuvant, notwithstanding the use of viscosity modifiers. Such processes also run the risk of exposing the active, i.e., a drug, or vitamin C, or other components to prolonged exposure to moisture and elevated temperatures, which may render it ineffective or even harmful.

In addition to the concerns associated with degradation of an active during extended exposure to moisture, the conventional drying methods themselves are unable to provide uniform films. The length of heat exposure during conventional processing, often referred to as the "heat history", and the manner in which such heat is applied, have a direct effect on the formation and morphology of the resultant film product. Uniformity is particularly difficult to achieve via conventional drying methods where a relatively thicker film, which is well-suited for the incorporation of a drug active, is desired. Thicker uniform films are more difficult to achieve because the surfaces of the film and the inner portions of the film do not experience the same external conditions simultaneously during drying. Thus, observation of relatively thick films made from such conventional processing shows a non-uniform structure caused by convection and intermolecular forces and requires greater than 10% moisture to remain flexible. The amount of free moisture can often interfere over time with the drug leading to potency issues and therefore inconsistency in the final product.

Conventional drying methods generally include the use of forced hot air using a drying oven, drying tunnel, and the like. The difficulty in achieving a uniform film is directly related to the rheological properties and the process of water evaporation in the film-forming composition. When the surface of an aqueous polymer solution is contacted with a high temperature air current, such as a film-forming composition passing through a hot air oven, the surface water is immediately evaporated forming a polymer film or skin on the surface. This seals the remainder of the aqueous film-forming composition beneath the surface, forming a barrier through which the remaining water must force itself as it is evaporated in order to achieve a dried film. As the temperature outside the film continues to increase, water vapor pressure builds up under the surface of the film, stretching the surface of the film, and ultimately ripping the film surface open allowing the water vapor to escape. As soon as the water vapor has escaped, the polymer film surface reforms, and this process is repeated, until the film is completely dried. The result of the repeated destruction and reformation of the film surface is observed as a "ripple effect" which produces an uneven, and therefore non-uniform film. Frequently, depending on the polymer, a surface will seal so tightly that the remaining water is difficult to remove, leading to very long drying times, higher temperatures, and higher energy costs.

Other factors, such as mixing techniques, also play a role in the manufacture of a pharmaceutical film suitable for commercialization and regulatory approval. Air can be trapped in the composition during the mixing process or later during the film making process, which can leave voids in the film product as the moisture evaporates during the drying stage. The film frequently collapse around the voids resulting in an uneven film surface and therefore, non-uniformity of the final film product. Uniformity is still affected even if the voids in the film caused by air bubbles do not collapse. This situation also provides a non-uniform film in that the spaces, which are not uniformly distributed, are occupying area that would otherwise be occupied by the film composition. None of the above-mentioned patents either addresses or proposes a solution to the problems caused by air that has been introduced to the film.

Therefore, there is a need for methods and compositions for film products, which use a minimal number of materials or components, and which provide a substantially non-self-aggregating uniform heterogeneity throughout the area of the films.

SUMMARY OF THE INVENTION

The present invention provides dissolvable films and methods of forming same. The films of the invention are produced through a selection of a pH modulated polymer system that reduces or prevents synerisis when combined in water with components having a non-neutral pH, such as active ions. Active ions, such as acids, bases or buffer systems, may be used to achieve delivery of a drug contained in the same film or a different film at a desired pH.

The films can be divided into equally sized units having substantially equal amounts of each compositional component present. This advantage is particularly useful because it permits large area films to be initially formed, and subsequently cut into individual units without concern for whether each unit is compositionally equal. For example, the films of the present invention have particular applicability as delivery systems for actives because each film unit will contain the proper amount of the active.

As used herein, the term "synerisis" is a process wherein a polymer recoils or separates from the water phase.

As used herein, the term "component having a non-neutral pH" is meant to include active ions that, when dissolved in water, give a solution with a pH of less than about 7 (acids) or greater than about 7 (bases). The term is also meant to include compositions of active ions, wherein the composition has a pH of less than about 7 or greater than about 7.

As used herein, the term "component having an acidic pH" and the like is meant to include active ions that, when dissolved in water, give a solution with a pH less than about 7. The term is also meant to include acidic compositions of active ion(s), wherein the composition has a pH of less than about 7.

As used herein, the term "component having a basic pH" is meant to include active agents that, when dissolved in water, give a solution with a pH greater than about 7. The term is also meant to include basic compositions of active ion(s), wherein the composition has a pH of greater than about 7.

In one embodiment, a pH modulated film in accordance with the present invention may be applied either directly or indirectly to an area of the skin. In other embodiments, the pH modulated film may be applied either directly or indirectly to mucosal areas of the body, such as the oral, vaginal and anal areas of the body. In still other embodiments, the pH modulated film may be applied either directly or indirectly to a hard surface, such as a particular surface area in need of cleaning.

A pH modulated film in accordance with the present invention may be used to achieve enhanced delivery of an active to a site in need thereof. For example, the pH modulated film may be used to enhance delivery of a drug contained in either the pH modulated film or a separate film used in conjunction with the pH modulated film.

In one aspect of the present invention, there is provided a composition, which may be in the form of a film. The composition includes at least one component having a non-neutral pH when combined with water; and a pH modulated polymer system selected to reduce or prevent synerisis when combined with the non-neutral component in combination with water. In particular, the present inventors have found that components that are acidic or basic in nature should be formulated into films using certain polymer systems in order to prevent the polymer from recoiling from the water phase causing synerisis. In some embodiments, the non-neutral component of the pH modulated film may be an active agent, such as a drug. However, in other embodiments, the non-neutral component(s) in the pH modulated film may be an acid component, a basic component, or a buffer system (acid/base system) used to modulate or maintain the pH of an active agent (e.g., a drug). The active agent may be contained in the pH modulated film or a separate film used in conjunction with the pH modulated film. In some embodiments, by modulating the pH of a drug delivery system, enhanced delivery of the drug may be achieved.

The present invention further provides a composition, which may be in the form of a film, that includes a component having an acidic pH when combined with water; and a polymer system including at least one neutral or acidic polymer.

Further provided is a composition, which may be in the form of a film, including a component having an acidic pH when combined with water; and a polymer system including a weak base; at least one neutral polymer; and a basic polymer.

Also provided is a composition, which may be in the form of a film, that includes a component having a basic pH when combined with water; and a polymer system including at least one basic polymer.

As will be described in further detail below, the pH modulated film is desirably substantially dissolvable when exposed to mucosal areas of the body, or to a wetting agent, such as water. Contacting the film with the mucosal area or wetting agent permits the components in the film to be dissolved or dispersed out of the film in the presence of an active agent. The active agent (e.g., a drug) may be included in the pH modulated film of the present invention or a separate water soluble film used in conjunction with the pH modulated film. The wetting agent may be placed on a substrate surface, including skin and wounds, and the film(s) placed on the wetted surface. Alternatively, the film(s) may be placed on the substrate surface, including skin and wounds, and subsequently hydrated.

Each of the films of the present invention may be divided into smaller individual film units, which may be sized and packaged to provide dosage units for consumption.

The present invention also provides a device that includes a film composition and a delivery substrate. The film composition includes a component having a non-neutral pH when combined with water; and a pH modulated polymer system selected to reduce or prevent synerisis when combined with the non-neutral component in combination with water. Delivery substrates may include, for example, tampons or bandages.

Also provided is a method of preparing the films of the present invention. The method includes providing a component having a non-neutral pH when combined with water; and providing a pH modulated polymer system selected to reduce or prevent synerisis when combined with the non-neutral component in combination with an aqueous solvent. The method further includes combining the non-neutral component and the polymer system with an aqueous solvent to produce a film-forming composition; and forming the film-forming composition into a film. The method may also involve removing the solvent through drying. Preferably, the drying is a controlled drying process, as described further herein.

The polymer may be selected in order to provide a viscosity that maintains a non-self-aggregating uniform heterogeneity. Various techniques may be used to form the film, including reverse roll coating, extrusion, deposition into molds, and other techniques.

Further provided is a method of topical administration of an active. This method involves providing a pH modulated film composition that includes (i) a component having a non-neutral pH when combined with water; and (ii) a polymer system selected to reduce or prevent synerisis when combined with the non-neutral component in combination with water. The method also includes applying the film to a body surface, such as a mucosal membrane or wound, in the presence of an active, such as a drug.

The present invention further provides a system for applying an active. This system includes a water soluble composition in the form of a first film, the composition including (i) at least one component having a non-neutral pH when combined with water; and (ii) a pH modulated polymer system selected to reduce or prevent synerisis when combined with the non-neutral component in combination with aqueous media. This system also includes an aqueous solvent for dissolving the water soluble first film. The solvent, which may be present in a container, is provided for direct contact with the first film to cause the non-neutral component to be dissolved or dispersed out of the first film in the presence of an active, whereby the active can be applied to a surface area in need thereof. The system may optionally include an applicator, such as a sponge applicator, for applying the active to the surface area in need thereof. The active to be delivered may be contained in the first film, or may be contained in a second water soluble film used in conjunction with the first film. The second film, when present, need not include the same combination of polymers as in the first film, but is desirably, but not necessarily, water soluble or partially water soluble in nature.

DETAILED DESCRIPTION OF THE INVENTION

Figure 1:
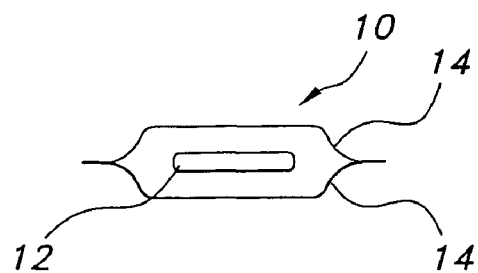
FIG. 1 shows a side view of a package containing a unit dosage film of the present invention.

The present invention is based, in part, on the inventors' discovery that components that are acidic or basic in nature have to be formulated into films using certain types of polymer systems. For example, an acidic composition performs well in a polymer system that includes a neutral polymer or acidic polymer. However, when an acidic composition is combined with basic charged polymers, it has been found that the polymer recoils from the water phase causing synerisis. On the other hand, the present inventors have found that a basic composition will not perform well in neutral or positive polymer systems, but works well in basic polymer systems.

Moreover, the present inventors have found that, when an acidic composition is combined with a complementary base in a neutral polymer system, this disadvantageously results in a collapse of the neutral polymer system. However, the addition of small amounts of modified basic polymers, such as polypropylene glycol alginate, protects the neutral polymer system and prevents synerisis.

In some embodiments of the present invention, the polymer system includes a buffer system to provide the film-forming composition with a substantially controlled pH. A neutral pH may be advantageous in certain instances because it substantially prevents drugs, which are mostly chemically weak acids or weak bases, from ionizing. The ionized form has an electric charge, and in this form, it typically cannot cross lipid membranes. Thus, by providing a substantially neutral pH environment, the drug is in an unionized form, which is lipid soluble and can cross membranes easily. However, at other times, a lower or higher pH may be necessary and require the use of a buffer to maintain a given pH. In some embodiments, a pH modulated film according to the present invention may be used to form a drug delivery system that yields a higher blood level of the drug relative to in the absence of the pH modulated film. A drug or other active agent may be contained in the pH modulated film, or in a separate film used in conjunction with the pH modulated film, the second film being desirably, but not necessarily, water-soluble or partially water-soluble. In some instances the second film may be substantially water-insoluble, but capable of releasing the drug. Upon contact of the film(s) with fluid, such as a bodily fluid or mucosal membrane, the components of the film(s) are dissolved and/or dispersed out therefrom to permit delivery of at least one active agent (e.g., a drug) at a desired pH.

Table 1 below is provided for purposes of illustrating various single film and two-film embodiments of the present invention, and is not intended to limit the invention in any way. With respect to the two-film embodiments shown in Table 1, the polymer combinations in these films may be the same or different polymer combinations. The active ions (e.g., acids, bases) in the respective films determine the selection of polymers. Also, while not shown in Table 1, each of the films, e.g. first and second films, may independently include an active. The actives may be the same or different. Additionally, more than one active may be present in any one film or film layer.

TABLE 1

SINGLE FILMS* polymer/active/acid ions
polymer/active/base ions
polymer/active/acid, buffer ions
polymer/active/base, buffer ions
polymer/active/acid, base ions
polymer/active/acid, base, buffer ions

MULTIPLE FILMS*

| First Film | Second Film |
| --- | --- |
| polymer/active | polymer/buffer ions |
| polymer/active | polymer/acid ions |
| polymer/active | polymer/base ions |
| polymer/active | polymer/acid, base ions |
| polymer/active/buffer ions | polymer/acid ions |
| polymer/active/buffer ions | polymer/base ions |
| polymer/active/acid ions | polymer/buffer ions |
| polymer/active/base ions | polymer/buffer ions |
| polymer/active/base, acid ions | polymer/buffer ions |

*The films include film-forming polymers.

Each of the films will include film-forming polymers. The table provides examples of some of the various combinations of ions and buffers which are intended to be included in the various embodiments of the invention.

For the purposes of the present invention, the term non-self-aggregating uniform heterogeneity refers to the ability of the films of the present invention, which are formed from one or more components in addition to a polar solvent, to provide a substantially reduced occurrence of, i.e. little or no, aggregation or conglomeration of components within the film as is normally experienced when films are formed by conventional drying methods, such as a high-temperature air-bath using a drying oven, drying tunnel, vacuum drier, or other such drying equipment. The term heterogeneity, as used in the present invention, includes films that will incorporate a single component, such as a polymer, as well as combinations of components, such as a polymer and an active. Uniform heterogeneity includes the substantial absence of aggregates or conglomerates as is common in conventional mixing and heat drying methods used to form films.

Furthermore, the films of the present invention may have a substantially uniform thickness, which is also not provided by the use of conventional drying methods used for drying water-based polymer systems. The absence of a uniform thickness detrimentally affects uniformity of component distribution throughout the area of a given film.

The film products of the present invention are produced by a combination of a properly selected polymer(s), a polar solvent and at least one non-neutral component, such as an acidic or basic component, as well as other fillers known in the art. In some embodiments, the films may further include active agents, such as drugs. The active agent may be the same or different from the non-neutral component. The films provide a non-self-aggregating uniform heterogeneity of the components within them by utilizing a selected casting or deposition method and a controlled drying process. Examples of controlled drying processes include, but are not limited to, the use of the apparatus disclosed in U.S. Pat. No. 4,631,837 to Magoon ("Magoon"), herein incorporated by reference, as well as hot air impingement across the bottom substrate and bottom heating plates. Another drying technique for obtaining the films of the present invention is controlled radiation drying, in the absence of uncontrolled air currents, such as infrared and radio frequency radiation (i.e. microwaves).

The objective of the drying process is to provide a method of drying the films that avoids complications, such as the noted "rippling" effect, that are associated with conventional drying methods and which initially dry the upper surface of the film, trapping moisture inside. In conventional oven drying methods, as the moisture trapped inside subsequently evaporates, the top surface is altered by being ripped open and then reformed.

These complications are avoided by the present invention, and a uniform film is provided by drying the bottom surface of the film first or otherwise preventing the formation of polymer film formation (skin) on the top surface of the film prior to drying the depth of the film. This may be achieved by applying heat to the bottom surface of the film with substantially no top air flow, or alternatively by the introduction of controlled microwaves to evaporate the water or other polar solvent within the film, again with substantially no top air flow.

Yet alternatively, drying may be achieved by using balanced fluid flow, such as balanced air flow, where the bottom and top air flows are controlled to provide a uniform film. In such a case, the air flow directed at the top of the film should not create a condition which would cause movement of particles present in the wet film, due to forces generated by the air currents.

Additionally, air currents directed at the bottom of the film should desirably be controlled such that the film does not lift up due to forces from the air. Uncontrolled air currents, either above or below the film, can create non-uniformity in the final film products. The humidity level of the area surrounding the top surface may also be appropriately adjusted to prevent premature closure or skinning of the polymer surface.

This manner of drying the films provides several advantages. Among these are the faster drying times and a more uniform surface of the film, as well as uniform distribution of components for any given area in the film. In addition, the faster drying time allows viscosity to quickly build within the film, further encouraging a uniform distribution of components and decrease in aggregation of components in the final film product. Desirably, the drying of the film will occur within about ten minutes or fewer, or more desirably within about five minutes or fewer.

The present invention yields exceptionally uniform film products when attention is paid to reducing the aggregation of the compositional components. By avoiding the introduction of and eliminating excessive air in the mixing process, selecting polymers and solvents to provide a controllable viscosity and by drying the film in a rapid manner from the bottom up, such films result.

The products and processes of the present invention rely on the interaction among various steps of the production of the films in order to provide films that substantially reduce the self-aggregation of the components within the films. Specifically, these steps include the particular method used to form the film, making the composition mixture to prevent air bubble inclusions, controlling the viscosity of the film forming composition and the method of drying the film. More particularly, a greater viscosity of components in the mixture is particularly useful when a film component, such as a drug active, is not soluble in the selected polar solvent in order to prevent it from settling out. However, the viscosity must not be too great as to hinder or prevent the chosen method of casting, which desirably includes reverse roll coating due to its ability to provide a film of substantially consistent thickness.

In addition to the viscosity of the film or film-forming components or matrix, there are other considerations taken into account by the present invention for achieving desirable film uniformity. For example, stable suspensions are achieved which prevent solid (such as drug particles) sedimentation in non-colloidal applications. One approach provided by the present invention is to balance the density of the particulate ($\rho_p$) and the liquid phase ($\rho_1$) and increase the viscosity of the liquid phase ($\mu$). For an isolated particle, Stokes law relates the terminal settling velocity (Vo) of a rigid spherical body of radius (r) in a viscous fluid, as follows:

$$V_o = (2gr^2)(\rho_p - \rho_1)/9\mu$$

At high particle concentrations, however, the local particle concentration will affect the local viscosity and density. The viscosity of the suspension is a strong function of solids volume fraction, and particle-particle and particle-liquid interactions will further hinder settling velocity.

Stokian analyses has shown that the incorporation of a third phase, dispersed air or nitrogen, for example, promotes suspension stability. Further, increasing the number of particles leads to a hindered settling effect based on the solids volume fraction. In dilute particle suspensions, the rate of sedimentation, v, can be expressed as:

$$v/V_o = 1/(1+\kappa\phi)$$

where $\kappa$ = a constant, and $\phi$ is the volume fraction of the dispersed phase. More particles suspended in the liquid phase results in decreased velocity. Particle geometry is also an important factor since the particle dimensions will affect particle-particle flow interactions.

Similarly, the viscosity of the suspension is dependent on the volume fraction of dispersed solids. For dilute suspensions of non-interaction spherical particles, an expression for the suspension viscosity can be expressed as:

$$\mu/\mu_o = 1 + 2.5\phi$$

where $\mu_o$ is the viscosity of the continuous phase and $\phi$ is the solids volume fraction. At higher volume fractions, the viscosity of the dispersion can be expressed as $$\mu/\mu_o = 2.5\phi + C_1\phi^2 + C_2\phi^3 +$$

where C is a constant.

The viscosity of the liquid phase is critical and is desirably modified by customizing the liquid composition to a viscoelastic non-Newtonian fluid with low yield stress values. This is the equivalent of producing a high viscosity continuous phase at rest. Formation of a viscoelastic or a highly structured fluid phase provides additional resistive forces to particle sedimentation. Further, flocculation or aggregation can be controlled minimizing particle-particle interactions. The net effect would be the preservation of a homogeneous dispersed phase.

The addition of hydrocolloids to the aqueous phase of the suspension increases viscosity, may produce viscoelasticity and can impart stability depending on the type of hydrocolloid, its concentration and the particle composition, geometry, size, and volume fraction. The particle size distribution of the dispersed phase needs to be controlled by selecting the smallest realistic particle size in the high viscosity medium, i.e., <500 µm. The presence of a slight yield stress or elastic body at low shear rates may also induce permanent stability regardless of the apparent viscosity. The critical particle diameter can be calculated from the yield stress values. In the case of isolated spherical particles, the maximum shear stress developed in settling through a medium of given viscosity can be given as $$\tau_{max} = 3V\mu/2r$$

For pseudoplastic fluids, the viscosity in this shear stress regime may well be the zero shear rate viscosity at the Newtonian plateau.

A stable suspension is an important characteristic for the manufacture of a pre-mix composition which is to be fed into the film casting machinery film, as well as the maintenance of this stability in the wet film stage until sufficient drying has occurred to lock-in the particles and matrix into a sufficiently solid form such that uniformity is maintained. For viscoelastic fluid systems, a rheology that yields stable suspensions for extended time period, such as 24 hours, must be balanced with the requirements of high-speed film casting operations. A desirable property for the films is shear thinning or pseudoplasticity, whereby the viscosity decreases with increasing shear rate. Time dependent shear effects such as thixotropy are also advantageous. Structural recovery and shear thinning behavior are important properties, as is the ability for the film to self-level as it is formed.

The rheology requirements for the inventive compositions and films are quite severe. This is due to the need to produce a stable suspension of particles, for example 30-60 wt %, in a viscoelastic fluid matrix with acceptable viscosity values throughout a broad shear rate range. During mixing, pumping, and film casting, shear rates in the range of $10$-$10^5$ sec.$^{-1}$ may be experienced and pseudoplasticity is the preferred embodiment.

In film casting or coating, rheology is also a defining factor with respect to the ability to form films with the desired uniformity. Shear viscosity, extensional viscosity, viscoelasticity, structural recovery will influence the quality of the film. As an illustrative example, the leveling of shear-thinning pseudoplastic fluids has been derived as $$\alpha^{(n-1/n)} = \alpha_o^{(n-1/n)} - ((n-1)/(2n-1))(\tau/K)^{1/n}(2\pi/\lambda)^{(3+n)/n}$$
$$h^{(2n+1)/n}t$$

where $\alpha$ is the surface wave amplitude, $\alpha_o$ is the initial amplitude, $\lambda$ is the wavelength of the surface roughness, and both "n" and "K" are viscosity power law indices. In this example, leveling behavior is related to viscosity, increasing as n decreases, and decreasing with increasing K.

Desirably, the films or film-forming compositions of the present invention have a very rapid structural recovery, i.e. as the film is formed during processing, it doesn't fall apart or become discontinuous in its structure and compositional uniformity. Such very rapid structural recovery retards particle settling and sedimentation. Moreover, the films or film-forming compositions of the present invention are desirably shear-thinning pseudoplastic fluids. Such fluids with consideration of properties, such as viscosity and elasticity, promote thin film formation and uniformity.

Thus, uniformity in the mixture of components depends upon numerous variables. As described herein, viscosity of the components, the mixing techniques and the rheological properties of the resultant mixed composition and wet casted film are important aspects of the present invention. Additionally, control of particle size and particle shape are further considerations. Desirably, the size of the particulate may be a particle size of 150 microns or less, for example 100 microns or less. Moreover, such particles may be spherical, substantially spherical, or non-spherical, such as irregularly shaped particles or ellipsoidally shaped particles. Ellipsoidally shaped particles or ellipsoids are desirable because of their ability to maintain uniformity in the film forming matrix as they tend to settle to a lesser degree as compared to spherical particles.

A number of techniques may be employed in the mixing stage to prevent bubble inclusions in the final film. To provide a composition mixture with substantially no air bubble formation in the final product, anti-foaming or surface-tension reducing agents may be employed. Additionally, the speed of the mixture is desirably controlled to prevent cavitation of the mixture in a manner which pulls air into the mix. Finally, air bubble reduction can further be achieved by allowing the mix to stand for a sufficient time for bubbles to escape prior to drying the film. Desirably, the inventive process first forms a masterbatch of film-forming components without active ingredients or volatile materials. In one embodiment, the active(s) are combined with smaller mixes of the masterbatch just prior to casting. Thus, the masterbatch pre-mix can be allowed to stand for a longer time without concern for instability of the active agent or other ingredients.

When the material is formed including the film-forming polymer and polar solvent in addition to any additives and the active ingredient, this may be done in a number of steps. For example, the ingredients may all be added together or a premix may be prepared. The advantage of a pre-mix is that all ingredients except for the active may be combined in advance, with the active added just prior to formation of the film. This is especially important for actives that may degrade with prolonged exposure to water, air or another polar solvent.

Figure 6:
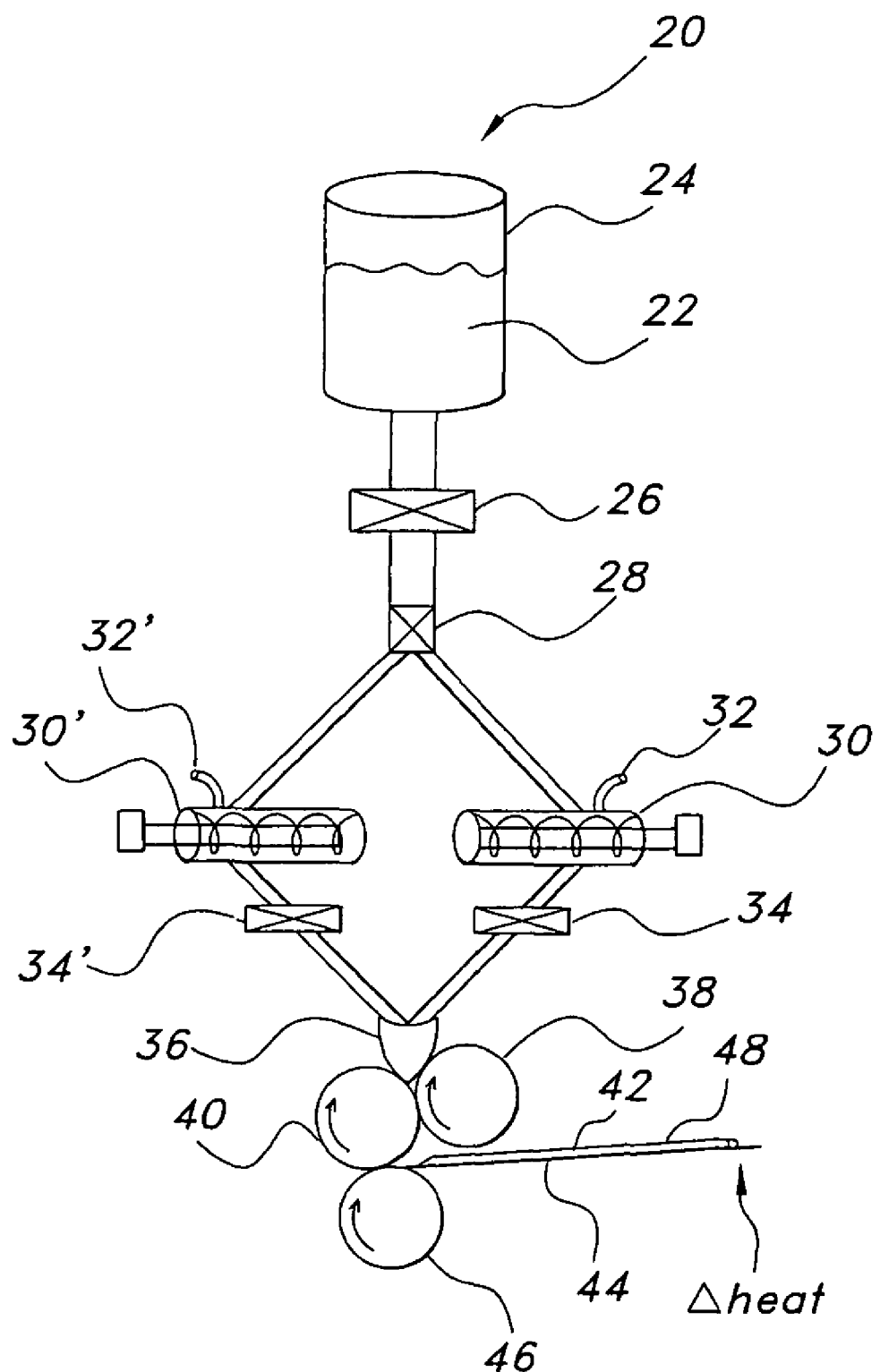
FIG. 6 is a schematic view of an apparatus suitable for preparation of a pre-mix, addition of an active, and subsequent formation of the film.

FIG. 6 shows an apparatus 20 suitable for the preparation of a pre-mix, addition of an active and subsequent formation of a film. The pre-mix or master batch 22, which includes the film-forming polymer, polar solvent, and any other additives except an active agent is added to the master batch feed tank 24. The components for pre-mix or master batch 22 are desirably formed in a mixer (not shown) prior to their addition into the master batch feed tank 24. Then a pre-determined amount of the master batch is controllably fed via a first metering pump 26 and control valve 28 to either or both of the first and second mixers, 30, 30'. The present invention, however, is not limited to the use of two mixers, 30, 30', and any number of mixers may suitably be used. Moreover, the present invention is not limited to any particular sequencing of the mixers 30, 30', such as parallel sequencing as depicted in FIG. 6, and other sequencing or arrangements of mixers, such as series or combination of parallel and series, may suitably be used. The required amount of the active or other ingredient is added to the desired mixer through an opening, 32, 32', in each of the mixers, 30, 30'. Desirably, the residence time of the pre-mix or master batch 22 is minimized in the mixers 30, 30'. While complete dispersion of the active into the pre-mix or master batch 22 is desirable, excessive residence times may result in leaching or dissolving of the active, especially in the case for a soluble drug active. Thus, the mixers 30, 30' are often smaller, i.e. lower residence times, as compared to the primary mixers (not shown) used in forming the pre-mix or master batch 22. After the active has been blended with the master batch pre-mix for a sufficient time to provide a uniform matrix, a specific amount of the uniform matrix is then fed to the pan 36 through the second metering pumps, 34, 34'. The metering roller 38 determines the thickness of the film 42 and applies it to the application roller. The film 42 is finally formed on the substrate 44 and carried away via the support roller 46.

While the proper viscosity uniformity in mixture and stable suspension of particles, and casting method are important in the initial steps of forming the composition and film to promote uniformity, the method of drying the wet film is also important. Although these parameters and properties assist uniformity initially, a controlled rapid drying process ensures that the uniformity will be maintained until the film is dry.

The wet film is then dried using controlled bottom drying or controlled microwave drying, desirably in the absence of external air currents or heat on the top (exposed) surface of the film 48 as described herein. Controlled bottom drying or controlled microwave drying advantageously allows for vapor release from the film without the disadvantages of the prior art. Conventional convection air drying from the top is not employed because it initiates drying at the top uppermost portion of the film, thereby forming a barrier against fluid flow, such as the evaporative vapors, and thermal flow, such as the thermal energy for drying. Such dried upper portions serve as a barrier to further vapor release as the portions beneath are dried, which results in non-uniform films. As previously mentioned some top air flow can be used to aid the drying of the films of the present invention, but it must not create a condition that would cause particle movement or a rippling effect in the film, both of which would result in non-uniformity. If top air is employed, it is balanced with the bottom air drying to avoid non-uniformity and prevent film lift-up on the carrier belt. A balance top and bottom air flow may be suitable where the bottom air flow functions as the major source of drying and the top air flow is the minor source of drying. The advantage of some top air flow is to move the exiting vapors away from the film thereby aiding in the overall drying process. The use of any top air flow or top drying, however, must be balanced by a number of factors including, but not limited, to rheological properties of the composition and mechanical aspects of the processing. Any top fluid flow, such as air, also must not overcome the inherent viscosity of the film-forming composition. In other words, the top air flow cannot break, distort or otherwise physically disturb the surface of the composition. Moreover, air velocities are desirably below the yield values of the film, i.e., below any force level that can move the liquids in the film-forming compositions. For thin or low viscosity compositions, low air velocity must be used. For thick or high viscosity compositions, higher air velocities may be used. Furthermore, air velocities are desirable low so as to avoid any lifting or other movement of the film formed from the compositions.

Moreover, the films of the present invention may contain particles that are sensitive to temperature, such as volatile ingredients, or drugs, which may have a low degradation temperature. In such cases, the drying temperature may be decreased while increasing the drying time to adequately dry the uniform films of the present invention. Furthermore, bottom drying also tends to result in a lower internal film temperature as compared to top drying. In bottom drying, the evaporating vapors more readily carry heat away from the film as compared to top drying which lowers the internal film temperature. Such lower internal film temperatures often result in decreased drug degradation and decreased loss of certain volatiles, such as flavors.

During film preparation, it may be desirable to dry films at high temperatures. High heat drying produces uniform films, and leads to greater efficiencies in film production. Films containing sensitive active components, however, may face degradation problems at high temperatures. Degradation is the "decomposition of a compound . . . exhibiting well-defined intermediate products." The American Heritage Dictionary of the English Language (4$^{th}$ ed. 2000). Degradation of an active component is typically undesirable as it may cause instability, inactivity, and/or decreased potency of the active component. For instance, if the active component is a drug or bioactive material, this may adversely affect the safety or efficacy of the final pharmaceutical product. Additionally, highly volatile materials will tend to be quickly released from this film upon exposure to conventional drying methods.

Degradation of an active component may occur through a variety of processes, such as, hydrolysis, oxidation, and light degradation, depending upon the particular active component. Moreover, temperature has a significant effect on the rate of such reactions. The rate of degradation typically doubles for every 10° C. increase in temperature. Therefore, it is commonly understood that exposing an active component to high temperatures will initiate and/or accelerate undesirable degradation reactions.

Proteins are one category of useful active agents that may degrade, denature, or otherwise become inactive when they are exposed to high temperatures for extended periods of time. Proteins serve a variety of functions in the body such as enzymes, structural elements, hormones and immunoglobulins. Examples of proteins include enzymes such as pancreatin, trypsin, pancrelipase, chymotrypsin, hyaluronidase, sutilains, streptokinaw, urokinase, altiplase, papain, bromelainsdiastase, structural elements such as collagen, elastin and albumin, hormones such as thyroliberin, gonadoliberin, adrenocorticottropin, corticotrophin, cosyntropin, sometrem, somatropion, prolactin, thyrotropin, somatostatin, vasopressin, felypressin, lypressin, insulin, glucagons, gastrin, pentagastrin, secretin, cholecystokinin-pancreozymin, and immunomodulators which may include polysaccharides in addition to glycoproteins including cytokines which are useful for the inhibition and prevention of malignant cell growth such as tumor growth. A suitable method for the production of some useful glycoproteins is disclosed in U.S. Pat. No. 6,281, 337 to Cannon-Carlson, et al., which in incorporated herein in its entirety.

Temperatures that approach 100° C. will generally cause degradation of proteins, certain peptides, as well as nucleic acids. For example, some glycoproteins will degrade if exposed to a temperature of 70° C. for thirty minutes. Proteins from bovine extract are also known to degrade at such low temperatures. DNA also begins to denature at this temperature.

Applicants have discovered, however, that the films of the present invention may be exposed to high temperatures during the drying process without concern for degradation, loss of activity, or excessive evaporation due to the inventive process for film preparation and forming. In particular, the films may be exposed to temperatures that would typically lead to degradation, denaturization, or inactivity of the active component, without causing such problems. According to the present invention, the manner of drying may be controlled to prevent deleterious levels of heat from reaching the active component.

As discussed herein, the flowable mixture is prepared to be uniform in content in accordance with the teachings of the present invention. Uniformity must be maintained as the flowable mass was formed into a film and dried. During the drying process of the present invention, several factors produce uniformity within the film while maintaining the active component at a safe temperature, i.e., below its degradation temperature. First, the films of the present invention have an extremely short heat history, usually only on the order of minutes, so that total temperature exposure is minimized to the extent possible. The films are controllably dried to prevent aggregation and migration of components, as well as preventing heat build up within. Desirably, the films are dried from the bottom. Controlled bottom drying, as described herein, prevents the formation of a polymer film, or skin, on the top surface of the film. As heat is conducted from the film bottom upward, liquid carrier, e.g., water, rises to the film surface. The absence of a surface skin permits rapid evaporation of the liquid carrier as the temperature increases, and thus, concurrent evaporative cooling of the film. Due to the short heat exposure and evaporative cooling, the film components such as drag or volatile actives remain unaffected by high temperatures. In contrast, skinning on the top surface traps liquid carrier molecules of increased energy within the film, thereby causing the temperature within the film to rise and exposing active components to high, potentially deleterious temperatures.

Second, thermal mixing occurs within the film due to bottom heating and absence of surface skinning. Thermal mixing occurs via convection currents in the film. As heat is applied to the bottom of the film, the liquid near the bottom increases in temperature, expands, and becomes less dense. As such, this hotter liquid rises and cooler liquid takes its place. While rising, the hotter liquid mixes with the cooler liquid and shares thermal energy with it, i.e., transfers heat. As the cycle repeats, thermal energy is spread throughout the film.

Robust thermal mixing achieved by the controlled drying process of the present invention produces uniform heat diffusion throughout the film. In the absence of such thermal mixing, "hot spots" may develop. Pockets of heat in the film result in the formation of particle aggregates or danger areas within the film and subsequent non-uniformity. The formation of such aggregates or agglomerations is undesirable because it leads to non-uniform films in which the active may be randomly distributed. Such uneven distribution may lead to large differences in the amount of active per film, which is problematic from a safety and efficacy perspective.

Furthermore, thermal mixing helps to maintain a lower overall temperature inside the film. Although the film surfaces may be exposed to a temperature above that at which the active component degrades, the film interior may not reach this temperature. Due to this temperature differential, the active does not degrade.

For instance, the films of the present invention desirably are dried for 10 minutes or less. Drying the films at 80° C. for 10 minutes produces a temperature differential of about 5° C. This means that after 10 minutes of drying, the temperature of the inside of the film is 5° C. less than the outside exposure temperature. In many cases, however, drying times of less than 10 minutes are sufficient, such as 4 to 6 minutes. Drying for 4 minutes may be accompanied by a temperature differential of about 30° C., and drying for 6 minutes may be accompanied by a differential of about 25° C. Due to such large temperature differentials, the films may be dried at efficient, high temperatures without causing heat sensitive actives to degrade.

Figure 7:
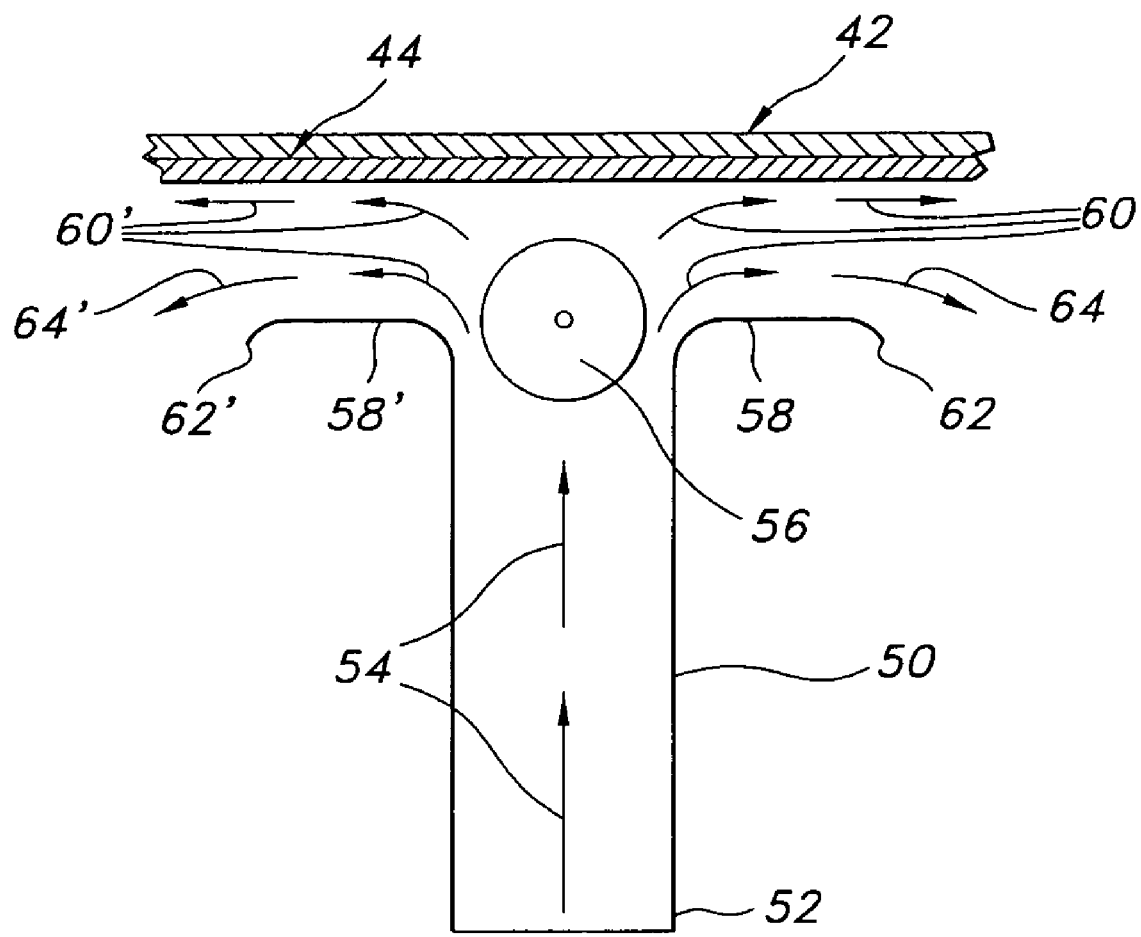
FIG. 7 is a schematic view of an apparatus suitable for drying the films of the present invention.
Figure 8:
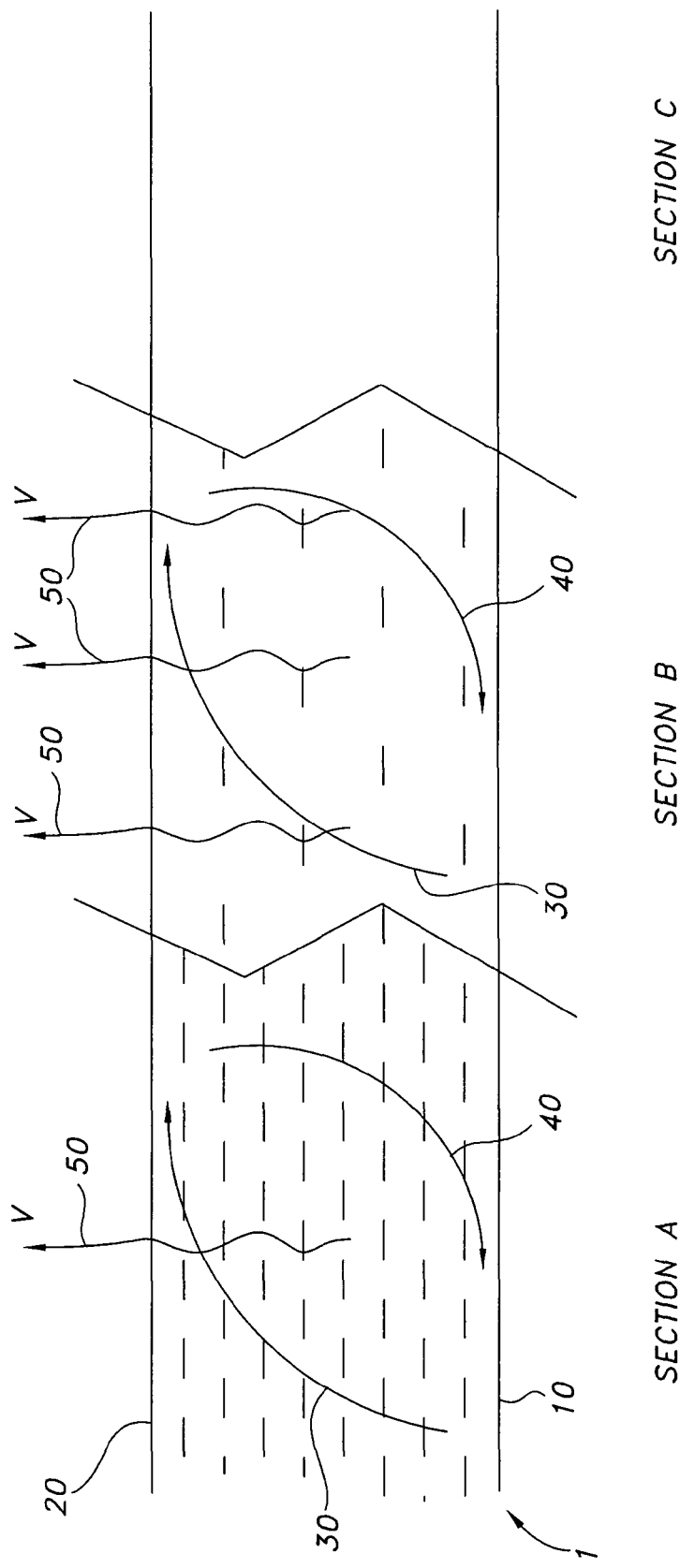
FIG. 8 is a sequential representation of the drying process of the present invention.

FIG. 8 is a sequential representation of the drying process of the present invention. After mechanical mixing, the film may be placed on a conveyor for continued thermal mixing during the drying process. At the outset of the drying process, depicted in Section A, the film 1 preferably is heated from the bottom 10 as it is travels via conveyor (not shown). Heat may be supplied to the film by a heating mechanism, such as, but not limited to, the dryer depicted in FIG. 7. As the film is heated, the liquid carrier, or volatile ("V"), begins to evaporate, as shown by upward arrow 50. Thermal mixing also initiates as hotter liquid, depicted by arrow 30, rises and cooler liquid, depicted by arrow 40, takes its place. Because no skin forms on the top surface 20 of the film 1, as shown in Section B the volatile liquid continues to evaporate 50 and thermal mixing 30/40 continues to distribute thermal energy throughout the film. Once a sufficient amount of the volatile liquid has evaporated, thermal mixing has produced uniform heat diffusion throughout the film 1. The resulting dried film 1 is a visco-elastic solid, as depicted in Section C. The components desirably are locked into a uniform distribution throughout the film. Although minor amounts of liquid carrier, i.e., water, may remain subsequent to formation of the visco-elastic, the film may be dried further without movement of the particles, if desired.

Furthermore, particles or particulates may be added to the film-forming composition or material after the composition or material is cast into a film. For example, particles may be added to the film 42 prior to the drying of the film 42. Particles may be controllably metered to the film and disposed onto the film through a suitable technique, such as through the use of a doctor blade (not shown), which is a device which marginally or softly touches the surface of the film and controllably disposes the particles onto the film surface. Other suitable, but non-limiting, techniques include the use of an additional roller to place the particles on the film surface, spraying the particles onto the film surface, and the like. The particles may be placed on either or both of the opposed film surfaces, i.e., the top and/or bottom film surfaces. Desirably, the particles are securely disposed onto the film, such as being embedded into the film. Moreover, such particles are desirably not fully encased or fully embedded into the film, but remain exposed to the surface of the film, such as in the case where the particles are partially embedded or partially encased. The particles may be any useful active(s), such as those described below.

Although the inventive process is not limited to any particular apparatus for the above-described desirable drying, one particular useful drying apparatus 50 is depicted in FIG. 7. Drying apparatus 50 is a nozzle arrangement for directing hot fluid, such as but not limited to hot air, towards the bottom of the film 42 which is disposed on substrate 44. Hot air enters the entrance end 52 of the drying apparatus and travels vertically upward, as depicted by vectors 54, towards air deflector 56. The air deflector 56 redirects the air movement to minimize upward force on the film 42. As depicted in FIG. 7, the air is tangentially directed, as indicated by vectors 60 and 60', as the air passes by air deflector 56 and enters and travels through chamber portions 58 and 58' of the drying apparatus 50. With the hot air flow being substantially tangential to the film 42, lifting of the film as it is being dried is thereby minimized. While the air deflector 56 is depicted as a roller, other devices and geometries for deflecting air or hot fluid may suitable be used. Furthermore, the exit ends 62 and 62' of the drying apparatus 50 are flared downwardly. Such downward flaring provides a downward force or downward velocity vector, as indicated by vectors 64 and 64', which tend to provide a pulling or drag effect of the film 42 to prevent lifting of the film 42. Lifting of the film 42 may not only result in non-uniformity in the film or otherwise, but may also result in non-controlled processing of the film 42 as the film 42 and/or substrate 44 lift away from the processing equipment.

Monitoring and control of the thickness of the film also contributes to the production of a uniform film by providing a film of uniform thickness. The thickness of the film may be monitored with gauges such as Beta Gauges. A gauge may be coupled to one or more other gauges at various points in the overall process including for example, at the end of the drying apparatus, i.e. drying oven or tunnel, to communicate through feedback loops to control and adjust the opening in the coating apparatus, the mixing steps, temperature, speed and other parameters important to uniformity of content in the final film, resulting in control of uniform film thickness.

The film products are generally formed by combining a properly selected polymer and polar solvent, as well as a component having a non-neutral pH when combined with water, or filler as desired. Optionally, the film components may be combined with an active agent, such as a drug, which may be the same or different from the non-neutral film component. Desirably, the solvent content of the combination may be at least about 30% by weight of the total combination. The material formed by this combination is formed into a film, desirably by roll coating, and then dried, desirably by a rapid and controlled drying process to maintain the uniformity of the film, more specifically, a non-self-aggregating uniform heterogeneity. The resulting film will desirably contain less than about 10% by weight solvent, more desirably less than about 8% by weight solvent, even more desirably less than about 6% by weight solvent and most desirably less than about 2%. The solvent may be water, a polar organic solvent including, but not limited to, ethanol, isopropanol, acetone, methylene chloride, or any combination thereof Consideration of the above discussed parameters, such as, but not limited to, rheology properties, viscosity, mixing method, casting method and drying method, also impact material selection for the different components of the present invention. Furthermore, such consideration with proper material selection provides the compositions of the present invention, including a pharmaceutical and/or cosmetic dosage form or film product having no more than a 10% variance of a pharmaceutical and/or cosmetic active per unit area. In other words, one aspect of the uniformity of the present invention relates to the presence of no more than a 10% by weight of pharmaceutical and/or cosmetic variance throughout the matrix. That is, the composed make-up of the film is uniform. Desirably, the variance is less than 5% by weight, less than 2% by weight, less than 1% by weight, or less than 0.5% by weight.

Film-Forming Polymers

The films of the present invention desirably include at least one water soluble polymer. The films may also include water swellable or water insoluble polymers, if desired. Specific examples of water insoluble polymers include, but are not limited to, ethyl cellulose, hydroxypropyl ethyl cellulose, cellulose acetate phthalate, hydroxypropyl methyl cellulose phthalate and combinations thereof.

In some embodiments, the film composition includes at least one component or composition having an acidic pH, and a polymer system that includes a neutral polymer or an acidic polymer.

Examples of neutral polymers include, but are not limited to, the following: hydroxyl methyl cellulose, hydroxyethyl cellulose, hydroxypropyl cellulose, hydroxypropylmethyl cellulose, polyethylene oxide, guar gum, locust bean gum, polydextrose, dextrin, dextran, pullulan, tamarine, starch and combinations thereof.

In some preferred embodiments, the polymer system includes a neutral polymer selected from the following: polyethylene oxides, cellulosic polymers and combinations thereof. For example, in one embodiment, the neutral polymer is a combination of hydroxypropyl methylcellulose and polyethylene oxide. In another embodiment, the neutral polymer is polyethylene oxide.

Suitable acidic polymers for use in the present invention include, but are not limited to the following: poly(glycolic acid) (PGA), poly(lactic acid) (PLA), polyanhydrides, sulfated carrageenan, furcelleran, xanthan and combinations thereof.

In further embodiments of the present invention, the non-neutral component or composition has a basic pH, and the polymer system with which it is combined in water is a basic polymer system. Suitable basic polymers for use in the present invention include, without limitation, the following: polyamino acids, polyaminocarbonates, polycarbonates, polyamides, carboxymethyl cellulose, alginates, carageenans, pectin, tragacanth, karaya and combinations thereof.

In some preferred embodiments, the basic polymer is an alginate polymer. One example of a modified alginate polymer is propylene glycol alginate.

In some embodiments of the present invention, the polymer system provides a neutral pH when combined with the non-neutral component or composition in combination with water. For example, the polymer system may include a buffer system. The present inventors have found that, when acidic components are combined with complementary bases in neutral polymer systems, this will cause a collapse of the neutral polymer system. However, the present inventors have also found that the addition of small amounts of basic polymers, or modified basic polymers, such as propylene glycol alginate, will protect the neutral polymer system and prevent synensis.

Thus, in one embodiment, the film composition includes at least one acidic compound or composition, and the polymer system includes a complementary weak base, a neutral polymer and a basic polymer. The basic polymer, such as an alginate polymer, protects the neutral polymer system, and prevents syneresis. In some other embodiments, the film composition includes at least one basic compound or composition, and the polymer system includes a complementary weak acid, a neutral polymer and a basic polymer, such as an alginate polymer.

As used herein, the phrase "water soluble polymer" and variants thereof refer to a polymer that is at least partially soluble in water, and desirably fully or predominantly soluble in water, or absorbs water. In some embodiments, the films of the present invention are at least partially dissolvable when exposed to a wetting agent or mucosal membrane. In some other embodiments, the inventive films are substantially dissolvable when exposed to a wetting agent or mucosal membrane. In some embodiments, a pH modulated film of the present invention may be used in conjunction with a second water soluble polymeric film, which may contain an active agent, such as a drug. The polymer combinations in these two films may be the same or different. However, both the pH modulated film and the second film are preferably water soluble in nature to permit delivery of active(s) associated with one or both films.

Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Polymers useful for incorporation into the films of the present invention include biodegradable polymers, copolymers, block polymers and combinations thereof. Among the known useful polymers or polymer classes which meet the above criteria are: poly(glycolic acid) (PGA), poly(lactic acid) (PLA), polydioxanoes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.).

The Biodel materials represent a family of various polyanhydrides which differ chemically.

Although a variety of different polymers may be used, it is desired to select polymers to reduce or prevent syneresis and to provide a desired viscosity of the mixture prior to drying. For example, if the film contains an acidic component or composition, a neutral polymer or acidic polymer is desired to prevent syneresis. Alternatively, if the film includes an acidic component or composition, it may be desirable to include a buffer system in the film composition, such as a weak base. It has been found by the present inventors that acids, and complementary bases, such as citric acid and sodium citrate, will cause a collapse of a neutral polymer system. Therefore, in this instance, the further addition of a basic polymer is desired to prevent syneresis. Also, if the film includes a basic component or composition, a basic polymer is desired to prevent syneresis.

If the film components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the topical agent in an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity of the film-forming matrix may be adjusted based on a selected active agent, depending on the other components within the matrix. For example, if a selected active agent, such as a drug, is not soluble within the selected solvent, a proper viscosity may be selected to prevent the drug active from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC, when used in combination, provide a flexible, strong film with the appropriate plasticity and elasticity for manufacturing and storage. No additional plasticizer or polyalcohol is needed for flexibility.

Additionally, polyethylene oxide (PEO), when used alone or in combination with a hydrophilic cellulosic polymer, achieves flexible, strong films. Additional plasticizers or polyalcohols are not needed for flexibility. Non-limiting examples of suitable cellulosic polymers for combination with PEO include HPC and HPMC. PEO and HPC have essentially no gelation temperature, while HPMC has a gelation temperature of 58-64° C. (Methocel EF available from Dow Chemical Co.). Moreover, these films are sufficiently flexible even when substantially free of organic solvents, which may be removed without compromising film properties. As such, if there is no solvent present, then there is no plasticizer in the films. PEO based films also exhibit good resistance to tearing, little or no curling, and fast dissolution rates when the polymer component contains appropriate levels of PEO.

To achieve the desired film properties, the level and/or molecular weight of PEO in the polymer component may be varied. Modifying the PEO content affects properties such as tear resistance, dissolution rate, and adhesion tendencies. Thus, one method for controlling film properties is to modify the PEO content. For instance, in some embodiments rapid dissolving films are desirable. By modifying the content of the polymer component, the desired dissolution characteristics can be achieved.

In accordance with the present invention, PEO desirably ranges from about 20% to 100% by weight in the polymer component. In some embodiments, the amount of PEO desirably ranges from about 1 mg to about 200 mg. The hydrophilic cellulosic polymer ranges from about 0% to about 80% by weight, or in a ratio of up to about 4:1 with the PEO, and desirably in a ratio of about 1:1.

In some embodiments, it may be desirable to vary the PEO levels to promote certain film properties. To obtain films with high tear resistance and fast dissolution rates, levels of about 50% or greater of PEO in the polymer component are desirable. To achieve adhesion prevention, i.e., preventing the film from adhering to the roof of the mouth, PEO levels of about 20% to 75% are desirable. In some embodiments, however, adhesion to the roof of the mouth may be desired, such as for administration to animals or children. In such cases, higher levels of PEO may be employed. More specifically, structural integrity and dissolution of the film can be controlled such that the film can adhere to mucosa and be readily removed, or adhere more firmly and be difficult to remove, depending on the intended use.

The molecular weight of the PEO may also be varied. High molecular weight PEO, such as about 4 million, may be desired to increase mucoadhesivity of the film. More desirably, the molecular weight may range from about 100,000 to 900,000, more desirably from about 100,000 to 600,000, and most desirably from about 100,000 to 300,000. In some embodiments, it may be desirable to combine high molecular weight (600,000 to 900,000) with low molecular weight (100,000 to 300,000) PEOs in the polymer component.

For instance, certain film properties, such as fast dissolution rates and high tear resistance, may be attained by combining small amounts of high molecular weight PEOs with larger amounts of lower molecular weight PEOs. Desirably, such compositions contain about 60% or greater levels of the lower molecular weight PEO in the PEO-blend polymer component.

To balance the properties of adhesion prevention, fast dissolution rate, and good tear resistance, desirable film compositions may include about 50% to 75% low molecular weight PEO, optionally combined with a small amount of a higher molecular weight PEO, with the remainder of the polymer component containing a hydrophilic cellulosic polymer (HPC or HPMC).

Controlled Release Films

The term "controlled release" is intended to mean the release of the active at a pre-selected or desired rate. For example, in embodiments where a medicament is included in the pH modulated film and/or in a separate film used in conjunction with the pH modulated film, it may be desirable to control its release from the film(s). This rate will vary depending upon the application. Desirable rates include fast or immediate release profiles as well as delayed, sustained or sequential release. Combinations of release patterns, such as initial spiked release followed by lower levels of sustained release of active are contemplated. Pulsed releases of the active are also contemplated.

The polymers that are chosen for the films of the present invention may also be chosen to allow for controlled disintegration of the active. This may be achieved by providing a substantially water insoluble film that incorporates an active that will be released from the film over time. This may be accomplished by incorporating a variety of different soluble or insoluble polymers and may also include biodegradable polymers in combination. Alternatively, coated controlled release active particles may be incorporated into a readily soluble film matrix to achieve the controlled release property of the active.

The convenience of administering a single dose of a medication, which releases actives in a controlled fashion over an extended period of time, as opposed to the administration of a number of single doses at regular intervals has long been recognized in the pharmaceutical arts. The advantage to the patient and clinician in having consistent and uniform levels of medication delivered to the body over an extended period of time are likewise recognized.

The actives employed in the present invention may be incorporated into the film compositions of the present invention in a controlled release form. For example, particles of a drug may be coated with polymers, such as ethyl cellulose or polymethacrylate, which are commercially available under brand names such as Aquacoat ECD and Eudragit E-100, respectively. Solutions of a drug may also be absorbed on such polymer materials and incorporated into the inventive film compositions. Other components may also be employed in such controlled release compositions.

Actives

When an active is introduced to the film, the amount of active per unit area is determined by the uniform distribution of the film. For example, when the films are cut into individual units, the amount of the active in the unit can be known with a great deal of accuracy. This is achieved because the amount of the active in a given area is substantially identical to the amount of active in an area of the same dimensions in another part of the film. The accuracy in dosage is particularly advantageous when the active is a medicament, i.e. a drug.

The actives that may be incorporated into the films of the present invention include, but are not limited to, pharmaceutical agents, cosmetic agents and cosmeceutical agents. It may be desirable to administer these agents at certain pH values to permit enhanced delivery of the agents across membranes. The present inventors have found that water soluble polymeric films including active ions, such as bases, acids, or buffer systems (acid/base systems) are useful in this regard, but that these active ions require selected pH modulated polymer systems in order to reduce or prevent synerisis in the film. Contacting the pH modulated film with the mucosal area or wetting agent permits the components in the film to be dissolved or dispersed out of the film in the presence of a pharmaceutical or other active agent, thereby achieving a desired pH for delivery thereof. The active agent may be included in the pH modulated film of the present invention or in a separate water soluble film used in conjunction with the pH modulated film.

As used herein, an active agent pertains to an agent or composition that may be applied to a particular surface area, such as, but not limited to, a certain area of the skin or mucosal tissue. The film, when used alone or in conjunction with another water soluble film, is used as a delivery system to carry an active to a particular surface area in need thereof. In some embodiments, the film compositions of the present invention may be applied to delivery substrates, such as tampons or bandages. For example, in one embodiment, a tampon is provided with two films where the first film includes a drug, and the second film is a pH modulated film including a buffer system. The second film permits the drug to cross vaginal membranes at a preferred pH.

In some embodiments, the polymeric film desirably includes at least one water soluble polymer. In some other embodiments, the film includes a combination of both water soluble and water insoluble polymers. When wetted, the dry film product at least partially solubilizes. Contacting the film product of the present invention with a wetting agent (e.g., water), or bodily fluid, or mucosal membrane permits the film components to be dissolved or dispersed out of the film in the presence of an active. The active may then be easily applied to a particular surface area, such as a skin area. As described above, the active agent may be included in the pH modulated film or in a separate water soluble film used in conjunction with the pH modulated film. For example, a separate water soluble film containing the active may be placed in contact with the pH modulated film, such that upon contact of the films with a wetting agent, such as a bodily fluid or mucosal membrane, the films will both solubilize, thereby releasing the active at a desired pH value.

In some embodiments, the wetting agent may be placed on a substrate surface, including skin and wounds, and the film placed on the wetted surface. Alternatively, the film may be placed on the substrate surface, including skin and wounds, and subsequently hydrated.

In some embodiments, a wetting agent (e.g., an aqueous solvent) may be dispensed from a container, the container being separate from or affixed to the film. For example, the container may be a pump bottle or sealed tube including the wetting agent.

Alternatively, the container may be a sealed, rupturable pouch including the wetting agent. Such a pouch may be separate from or affixed to the film. When the pouch is ruptured, the wetting agent may be brought into direct contact with the film to cause the film components to be dissolved out or dispersed out of the film, whereby the components, such as an active, can be applied to the substrate surface.

The film may be interposed between a container including the solvent and a substrate surface, including skin and wounds. Alternatively, the film may be interposed between a container including the solvent and an applicator.

For example, in some embodiments, a system useful for applying an active includes a water soluble polymeric film including at least one component having a non-neutral pH; a pH modulated polymer system selected to reduce synerisis when combined with the non-neutral component in combination with water; and a solvent for dissolving the film in the presence of an active. The active may be included in the same film or a different water soluble film with which it is in contact. The system may further include an applicator for applying the active to the substrate surface once it is released from the film. In some embodiments, the applicator is a sponge applicator. The film may be deposited on top of a wetted sponge applicator. Alternatively, the film may be deposited on top of a dry sponge applicator, which is subsequently wetted by water, body fluids or other solvents or other transferring substrate or device.

When optional active(s) are combined with the polymer(s) in the solvent to form the pH modulated film, the type of material that is formed depends on the solubilities of the actives and the polymer(s). If the active and/or polymer(s) are soluble in the selected solvent, this may form a solution. However, if the components are not soluble, the material that is formed may be classified as an emulsion, a colloid, or a suspension.

A wide variety of medicaments, bioactive active substances and pharmaceutical compositions may be included in the dosage forms of the present invention. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflanmmatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety a gents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and antithyroid preparations, diuretics, anti-spasmodics, terine relaxants, anti-obesity drugs, erythropoietic drugs, antiasthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (available as Oxycontin®), ibuprofen, aspirin, acetaminophen, and combinations thereof that may optionally include caffeine. Opiate agonists and antagonists, such as bupermorphine and naloxone are further examples of drugs for use in the present invention.

Other preferred drugs for other preferred active ingredients for use in the present invention include anti-diarrheals such as immodium AD, anti-histamines, anti-tussives, decongestants, vitamins, and breath fresheners. Common drugs used alone or in combination for . colds, pain, fever, cough, congestion, runny nose and allergies, such as acetaminophen, ibuprofen, chlorpheniramine maleate, dextromethorphan, dextromethorphan HBr, pseudoephedrine HCl, diphenhydramine and combinations thereof, such as dextromethorphan HBr and phenylephrine HCl (available as Triaminic®) may be included in the film compositions of the present invention.

Also contemplated for use herein are anxiolytics such as alprazolam (available as Xanax®); anti-psychotics such as clozopin (available as Clozaril®) and haloperidol (available as Haldol®); non-steroidal anti-inflammatories (NSAID's) such as dicyclofenacs (available as Voltaren®) and etodolac (available as Lodine®), anti-histamines such as diphenhydramine HCl (available as Benadryl® and TheraFlu®), loratadine (available as Claritin®), astemizole (available as Hismanal™), nabumetone (available as Relafen®), and Clemastine (available as Tavist®); anti-emetics such as granisetron hydrochloride (available as Kytril®) and nabilone (available as Cesamet™); bronchodilators such as Bentolin®, albuterol sulfate (available as Proventil®); anti-depressants such as fluoxetine hydrochloride (available as Prozac®), sertraline hydrochloride (available as Zoloft®), and paroxtine hydrochloride (available as Paxil®D); anti-tussives such as guaifensin; anti-migraines such as Imigra®; ACE-inhibitors such as enalaprilat (available as Vasotec®), captopril (available as Capoten®) and lisinopril (available as Zestril®); anti-Alzheimer's agents, such as nicergoline; $Ca^H$-antagonists such as nifedipine (available as Procardia® and Adalat®), and verapamil hydrochloride (available as Calan®); and sedative/hypnotics such as zaleplon (available as Sonata®) and eszopiclone (available as Lunesta®).

Erectile dysfunction therapies include, but are not limited to, drugs for facilitating blood flow to the penis, and for effecting autonomic nervous activities, such as increasing parasympathetic (cholinergic) and decreasing sympathetic (adrenersic) activities. Useful non-limiting drugs include sildenafils, such as Viagra®, tadalafils, such as Cialis®, vardenafils, apomorphines, such as Uprima®, yohimbine hydrochlorides such as Aphrodyne®, and alprostadils such as Caverject®.

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

Cosmetic and cosmeceutical agents include, but are not limited to, the following: moisturizers, shampoos, sunscreens and sun-blocking cosmetics, hair rinses, hair conditioners, wetting agents, fatting agents, RETIN-A, DIFFERIN, AVITA, BOTOX, MYOBLOC, proteins, peptides, fatty acids and antimicrobials.

An anti-oxidant may also be added to the film to prevent the degradation of an active, especially where the active is photosensitive.

Color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Moreover, fragrances can be included in the films. These may include extracts derived from plants, leaves, flowers, fruits and combinations thereof, for example.

Further Actives

In addition to cosmetic agents, cosmeceutical agents, and pharmaceutical agents, the term "active" may be any agent that can be applied to a particular surface area or ingested systemically. For example, an active may be a cleaning agent that can be applied to substrate in need of cleaning. Many of these cleaning agents are acidic or basic in nature and may be considered to be components having a non-neutral pH. For example, organic acids, including acetic, oxalic, hydroxyacetic and citric, may be used in cleaning compositions. Moreover, alkalis, such as sodium or potassium hydroxide, or alkaline salts such as sodium carbonate, may be employed in cleaning compositions. Such agents may be employed into the films provided herein using certain pH modulated polymer systems in order to reduce or prevent synerisis.

Dosages

The film products of the present invention are capable of accommodating a wide range of amounts of the active. The films are capable of providing an accurate dosage amount (determined by the size of the film and concentration of the active in the original polymer/water combination) regardless of whether the required dosage is high or extremely low. Therefore, depending on the type of active(s) that is incorporated into the film, the active amount may be as high as about 300 mg, desirably up to about 150 mg, or as low as the microgram range, or any amount therebetween.

The film products and methods of the present invention are well suited for high potency, low dosage drugs. This is accomplished through the high degree of uniformity of the films. Therefore, low dosage drugs, particularly more potent racemic mixtures of actives are desirable.

Anti-foaming and De-foaming Compositions

Anti-foaming and/or de-foaming components may also be used with the films of the present invention. These components aid in the removal of air, such as entrapped air, from the film-forming compositions. As described above, such entrapped air may lead to non-uniform films. Simethicone is one particularly useful anti-foaming and/or de-foaming agent. The present invention, however, is not so limited and other anti-foam and/or de-foaming agents may suitable be used.

Simethicone is generally used in the medical field as a treatment for gas or colic in babies. Simethicone is a mixture of fully methylated linear siloxane polymers containing repeating units of polydimethylsiloxane which is stabilized with trimethylsiloxy end-blocking unites, and silicon dioxide. It usually contains 90.5-99% polymethylsiloxane and 4-7% silicon dioxide. The mixture is a gray, translucent, viscous fluid which is insoluble in water.

When dispersed in water, simethicone will spread across the surface, forming a thin film of low surface tension. In this way, simethicone reduces the surface tension of bubbles air located in the solution, such as foam bubbles, causing their collapse. The function of simethicone mimics the dual action of oil and alcohol in water. For example, in an oily solution any trapped air bubbles will ascend to the surface and dissipate more quickly and easily, because an oily liquid has a lighter density compared to a water solution. On the other hand, an alcohol/water mixture is known to lower water density as well as lower the water's surface tension. So, any air bubbles trapped inside this mixture solution will also be easily dissipated. Simethicone solution provides both of these advantages. It lowers the surface energy of any air bubbles that trapped inside the aqueous solution, as well as lowering the surface tension of the aqueous solution. As the result of this unique functionality, simethicone has an excellent anti-foaming property that can be used for physiological processes (anti-gas in stomach) as well as any for external processes that require the removal of air bubbles from a product.

In order to prevent the formation of air bubbles in the films of the present invention, the mixing step can be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of simethicone into the film-forming composition either substantially reduces or eliminates the formation of air bubbles.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

Optional Components

A variety of other components and fillers may also be added to the films of the present invention. These may include, without limitation, surfactants; plasticizers which assist in compatibilizing the components within the mixture; polyalcohols; anti-foaming agents, such as silicone-containing compounds, which promote a smoother film surface by releasing oxygen from the film; and thermo-setting gels such as pectin, carageenan, and gelatin, which help in maintaining the dispersion of components.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water soluble polysaccharides such as alginates, carrageenans, guar gum, agar-agar, xanthan gum, gellan gum, gum arabic and related gums (gum ghatti, gum karaya, gum tragancanth), pectin, water soluble derivatives of cellulose: alkylcelluloses hydroxyalkylcelluloses and hydroxyalkylalkylcelluloses, such as methylcellulose, hydroxyniethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quatemized if desired; and other similar polymers.

Such extenders may optionally be added in any desired amount desirably within the range of up to about 80%, desirably about 3% to 50% and more desirably within the range of 3% to 20% based on the weight of all components.

Further additives may be inorganic fillers, such as the oxides of magnesium aluminum, silicon, titanium, etc. desirably in a concentration range of about 0.02% to about 3% by weight and desirably about 0.02% to about 1% based on the weight of all components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the flow properties of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about 5% and preferably within the range of about 0.5% to about 2% by weight of the total composition It is further useful to add silicon dioxide, calcium silicate, or titanium dioxide in a concentration of about 0.02% to about 1% by weight of the total composition. These compounds act as texturizing agents.

These additives are to be used in amounts sufficient to achieve their intended purpose. Generally, the combination of certain of these additives will alter the overall release profile of the active ingredient and can be used to modify, i.e. impede or accelerate the release.

Lecithin is one surface active agent for use in the present invention. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

As additional modifiers which enhance the procedure and product of the present invention are identified, Applicants intend to include all such additional modifiers within the scope of the invention claimed herein.

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Further potential additives include solubility enhancing agents, such as substances that form inclusion compounds with active components. Such agents may be useful in improving the properties of very insoluble and/or unstable actives. In general, these substances are doughnut-shaped molecules with hydrophobic internal cavities and hydrophilic exteriors. Insoluble and/or instable actives may fit within the hydrophobic cavity, thereby producing an inclusion complex, which is soluble in water. Accordingly, the formation of the inclusion complex permits very insoluble and/or instable actives to be dissolved in water. A particularly desirable example of such agents are cyclodextrins, which are cyclic carbohydrates derived from starch. Other similar substances, however, are considered well within the scope of the present invention.

Forming the Film

The films of the present invention must be formed into a sheet prior to drying. After the desired components are combined to form a multi-component matrix, including the polymer, water, and a non-neutral component or other components (e.g., an active agent) as desired, the combination is formed into a sheet or film, by any method known in the art such as extrusion, coating, spreading, casting or drawing the multi-component matrix. If a multi-layered film is desired, this may be accomplished by co-extruding more than one combination of components which may be of the same or different composition. A multi-layered film may also be achieved by coating, spreading, or casting a combination onto an already formed film layer.

Although a variety of different film-forming techniques may be used, it is desirable to select a method that will provide a flexible film, such as reverse roll coating. The flexibility of the film allows for the sheets of film to be rolled and transported for storage or prior to being cut into individual dosage forms. Desirably, the films will also be self-supporting or in other words able to maintain their integrity and structure in the absence of a separate support. Furthermore, the films of the present invention may be selected of materials that are edible or ingestible.

Casting the Film Composition

The invention uses processes for making self-supporting films having a substantially uniform distribution of components. The self supporting film is particularly useful for delivery of actives as discussed herein. The processes for making the film are designed to maintain the compositional uniformity of components distributed throughout the film, which is particularly necessary when actives, such as pharmaceutical actives, are incorporated into the film. In the pharmaceutical context, it is essential that the film is compositionally uniform so that it can be divided into individual film dosage units, each dosage unit having the appropriate amount of active when administered, such that regulatory approval can be secured.

One process used to make the films is described in U.S. application Ser. No. 10/074,272, which is incorporated in its entirety herein by reference. In this process, the films are prepared by rapidly forming a visco-elastic film by applying hot air currents to the film to prevent flow migration and intermolecular forces from creating aggregates or conglomerates thereby maintaining compositional uniform distribution of components in the film; and further drying the visco-elastic film to form a self-supporting film.

Desirably, the hot air currents are applied to the bottom of the film, with substantially no top air flow. This allows the depth of the film to be dried prior to forming a polymer skin on the top surface of the film, which would disrupt the surface of the film, leading to non-uniformity. The dried, self-supporting film is uniform in the distribution of the components contained therein, weight and thickness.

The film first may be fed onto the top side of a surface prior to the application of hot air currents. The wet film is desirably formed from a deaerated matrix within a time period before the active contained therein degrades. The hot air currents may then be applied to the bottom side of the surface with substantially no top air flow. The process may further include a step of dividing the dried film into individual dosage units of equal dimensions and compositional make-up. The hot air currents may be applied to the bottom surface of the film at a higher velocity than to the top surface of the film during drying. Hot air currents applied to dry the top of the films are less than that which would cause surface rippling or skinning. This permits the film to sufficiently thicken in viscosity to lock-in volumetric uniformity while permitting evaporation of water through the non-skinned surface.

The process may further include the preliminary steps of forming a masterbatch premix of an edible water-soluble polymer and water; deaerating the premix by mixing; feeding a predetermined amount of the deaerated premix to at least one mixer; adding an active component to the mixer; and mixing the components to achieve a uniform distribution thereof. Thereafter, the wet film is formed and dried.

Coating or casting methods are particularly useful for the purpose of forming the films of the present invention. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the simple process of immersion or dip coating, the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating is 100% solids, the process is termed "Extrusion" and in this case, the line speed is frequently much faster than the speed of the extrusion. This enables coatings to be considerably thinner than the width of the slot.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

Extruding the Film Composition

It may be particularly desirable to employ extrusion methods for forming film compositions containing PEO polymer components. These compositions contain PEO or PEO blends in the polymer component, and may be essentially free of added plasticizers, and/or surfactants, and polyalcohols.

The compositions may be extruded as a sheet at processing temperatures of less than about 90° C. Extrusion may proceed by squeezing the film composition through rollers or a die to obtain a uniform matrix. The extruded film composition then is cooled by any mechanism known to those of ordinary skill in the art. For example, chill rollers, air cooling beds, or water cooling beds may be employed. The cooling step is particularly desirable for film compositions containing PEO polymer components because PEO tends to hold heat. The thus formed sheets can be formed into various shapes, as desired.

Drying the Film

The drying step is also a contributing factor with regard to maintaining the uniformity of the film composition. A controlled drying process is particularly important when, in the absence of a viscosity increasing composition or a composition in which the viscosity is controlled, for example by the selection of the polymer, the components within the film may have an increased tendency to aggregate or conglomerate. An alternative method of forming a film with an accurate dosage, that would not necessitate the controlled drying process, would be to cast the films on a predetermined well. With this method, although the components may aggregate, this will not result in the migration of the active to an adjacent dosage form, since each well may define the dosage unit per se.

When a controlled or rapid drying process is desired, this may be through a variety of methods. A variety of methods may be used including those that require the application of heat. The liquid carriers are removed from the film in a manner such that the uniformity, or more specifically, the non-self-aggregating uniform heterogeneity, that is obtained in the wet film is maintained.

Desirably, the film is dried from the bottom of the film to the top of the film. Desirably, substantially no air flow is present across the top of the film during its initial setting period, during which a solid, visco-elastic structure is formed. This can take place within the first few minutes, e.g. about the first 0.5 to about 4.0 minutes of the drying process. Controlling the drying in this manner, prevents the destruction and reformation of the film's top surface, which results from conventional drying methods. This is accomplished by forming the film and placing it on the top side of a surface having top and bottom sides. Then, heat is initially applied to the bottom side of the film to provide the necessary energy to evaporate or otherwise remove the liquid carrier. The films dried in this manner dry more quickly and evenly as compared to air-dried films, or those dried by conventional drying means. In contrast to an air-dried film that dries first at the top and edges, the films dried by applying heat to the bottom dry simultaneously at the center as well as at the edges. This also prevents settling of ingredients that occurs with films dried by conventional means.

The temperature at which the films are dried is about 100° C. or less, desirably about 90° C. or less, and most desirably about 80° C. or less.

In some embodiments, the weight of the polar solvent is at least about 30% of the film before drying. In some other embodiments, the drying of the film reduces the weight percent of the polar solvent to about 10% or less. Preferably, the drying occurs within about 10 minutes or fewer.

Another method of controlling the drying process, which may be used alone or in combination with other controlled methods as disclosed above includes controlling and modifying the humidity within the drying apparatus where the film is being dried. In this manner, the premature drying of the top surface of the film is avoided.

Additionally, it has also been discovered that the length of drying time can be properly controlled, i.e. balanced with the heat sensitivity and volatility of the components, and particularly the flavor oils and drugs. The amount of energy, temperature and length and speed of the conveyor can be balanced to accommodate such actives and to minimize loss, degradation or ineffectiveness in the final film.

A specific example of an appropriate drying method is that disclosed by Magoon. Magoon is specifically directed toward a method of drying fruit pulp. However, the present inventors have adapted this process toward the preparation of thin films.

The method and apparatus of Magoon are based on an interesting property of water. Although water transmits energy by conduction and convection both within and to its surroundings, water only radiates energy within and to water. Therefore, the apparatus of Magoon includes a surface onto which the fruit pulp is placed that is transparent to infrared radiation. The underside of the surface is in contact with a temperature controlled water bath. The water bath temperature is desirably controlled at a temperature slightly below the boiling temperature of water. When the wet fruit pulp is placed on the surface of the apparatus, this creates a "refractance window." This means that infrared energy is permitted to radiate through the surface only to the area on the surface occupied by the fruit pulp, and only until the fruit pulp is dry. The apparatus of Magoon provides the films of the present invention with an efficient drying time reducing the instance of aggregation of the components of the film.

Another method of controlling the drying process involves a zone drying procedure. A zone drying apparatus may include a continuous belt drying tunnel having one or more drying zones located within. The conditions of each drying zone may vary, for example, temperature and humidity may be selectively chosen. It may be desirable to sequentially order the zones to provide a stepped up drying effect.

The speed of the zone drying conveyor desirably is continuous. Alternatively, the speed may be altered at a particular stage of the drying procedure to increase or decrease exposure of the film to the conditions of the desired zone. Whether continuous or modified, the zone drying dries the film without surface skinning.

Figure 9:
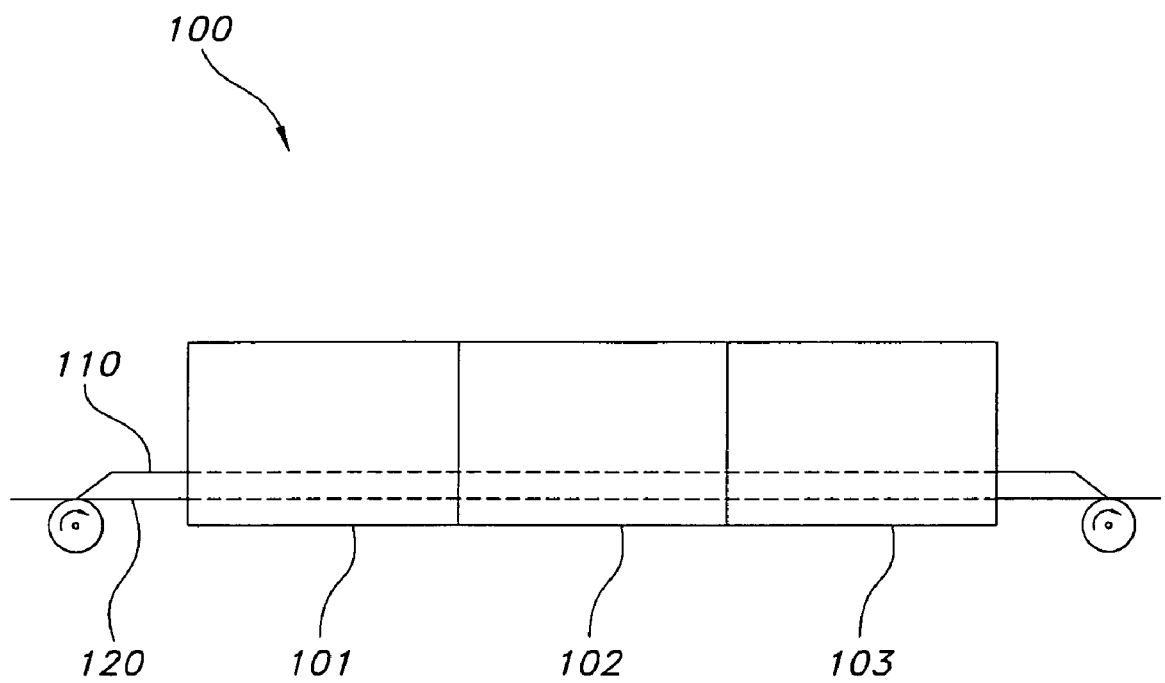
FIG. 9 is a schematic representation of a continuously-linked zone drying apparatus in accordance with the present invention.
Figure 10:
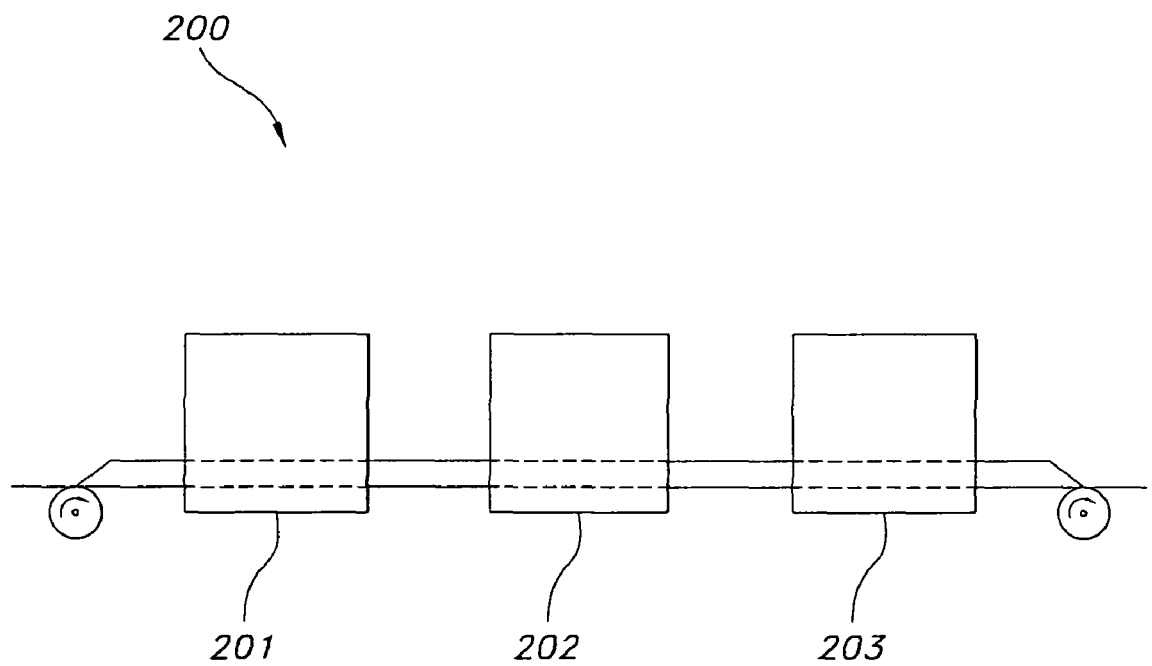
FIG. 10 is a schematic representation of a separate zone drying apparatus in accordance with the present invention.

According to an embodiment of the zone drying apparatus 100, shown in FIG. 9, the film 110 may be fed onto the continuous belt 120, which carries the film through the different drying zones. The first drying zone that the film travels through 101 may be a warm and humid zone. The second zone 102 may be hotter and drier, and the third zone 103 may also be hot and dry. These different zones may be continuous, or alternatively, they may be separated, as depicted by the zone drying apparatus 200 in FIG. 10, where the first drying zone 201, second drying zone 202 and third drying zone 203 are shown. The zone drying apparatus, in accordance with the present invention, is not limited to three drying zones. The film may travel through lesser or additional drying zones of varying heat and humidity levels, if desired, to produce the controlled drying effect of the present invention.

To further control temperature and humidity, the drying zones may include additional atmospheric conditions, such as inert gases. The zone drying apparatus further may be adapted to include additional processes during the zone drying procedure, such as, for example, spraying and laminating processes, so long as controlled drying is maintained in accordance with the invention.

The films may initially have a thickness of about 500 µm to about 1,500 µm, or about 20 mils to about 60 mils, and when dried have a thickness from about 3 µm to about 250 µm, or about 0.1 mils to about 10 mils. In some embodiments, the film product has a thickness of greater than 0.1 mils. In some other embodiments, the film product has a thickness of about 10 mils or fewer. In some further embodiments, the film product has a thickness of about 0.5 mils to about 5 mils. Desirably, the dried films will have a thickness of about 2 mils to about 8 mils, and more desirably, from about 3 mils to about 6 mils.

Testing Films for Uniformity

It may be desirable to test the films of the present invention for chemical and physical uniformity during the film manufacturing process. In particular, samples of the film may be removed and tested for uniformity in film components between various samples. Film thickness and over all appearance may also be checked for uniformity. Uniform films are desired, particularly for films containing pharmaceutical or cosmeceutical active components for safety and efficacy reasons.

A method for testing uniformity in accordance with the present invention includes conveying a film through a manufacturing process. This process may include subjecting the film to drying processes, dividing the film into individual dosage units, and/or packaging the dosages, among others. As the film is conveyed through the manufacturing process, for example on a conveyor belt apparatus, it is cut widthwise into at least one portion. The at least one portion has opposing ends that are separate from any other film portion. For instance, if the film is a roll, it may be cut into separate sub-rolls. Cutting the film may be accomplished by a variety of methods, such as with a knife, razor, laser, or any other suitable means for cutting a film.

The cut film then may be sampled by removing small pieces from each of the opposed ends of the portion(s), without disrupting the middle of the portion(s). Leaving the middle section intact permits the predominant portion of the film to proceed through the manufacturing process without interrupting the conformity of the film and creating sample-inducted gaps in the film. Accordingly, the concern of missing doses is alleviated as the film is further processed, e.g., packaged. Moreover, maintaining the completeness of cut portions or sub-rolls throughout the process will help to alleviate the possibility of interruptions in further film processing or packaging due to guilty control issues, for example, alarm stoppage due to notice of missing pieces.

After the end pieces, or sampling sections, are removed from the film portion(s), they may be tested for uniformity in the content of components between samples. Any conventional means for examining and testing the film pieces may be employed, such as, for example, visual inspection, use of analytical equipment, and any other suitable means known to those skilled in the art. If the testing results show non-uniformity between film samples, the manufacturing process may be altered. This can save time and expense because the process may be altered prior to completing an entire manufacturing run. For example, the drying conditions, mixing conditions, compositional components and/or film viscosity may be changed. Altering the drying conditions may involve changing the temperature, drying time, moisture level, and dryer positioning, among others.

Moreover, it may be desirable to repeat the steps of sampling and testing throughout the manufacturing process. Testing at multiple intervals may ensure that uniform film dosages are continuously produced. Alterations to the process can be implemented at any stage to minimize non-uniformity between samples.

In some embodiments, the method for testing uniformity in a film manufacturing process includes conveying a film having a length and a width through a manufacturing process; and cutting the film across the width into at least one portion having separate opposed ends and a central section during the manufacturing process. This testing method further includes removing samples of the film from each of the opposed ends of the at least one portion without disrupting the central section. Moreover, this method includes measuring the removed samples for compositional content or physical characteristics; and comparing the measured samples to determine their relative uniformity in their respective measurements.

Uses of Thin Films

The thin films of the present invention are well suited for many uses. The high degree of uniformity of the components of the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of an active to skin and other body surfaces, including those with mucous membranes.

Although it is not necessary to include an active, the films may be used to administer an active either topically or systemically. The pH modulated film may contain an active. Alternatively, or in addition, a separate water soluble film used in conjunction with the pH modulated film may contain an active. The films may include the same or different film-forming polymers. In one example, delivery of an active may be accomplished by preparing the film as described above and applying the film to a body surface of a mammal. In some embodiments, the body surface is a mucosal membrane, including without limitation orally, vaginally, an open wound, nasally, periodontically, rectally, opthalamically and optically or auricularly.

For example, the inventive films, either alone or in combination with a second water soluble film, may be useful for vaginal delivery of drugs. The vagina is a favorable site for both local and systemic delivery of drugs. For example, the vaginal cavity has been used for the delivery of locally acting drugs, such as antibacterial, antifungal, antiprotozoal, antiviral, labor-inducing and spermicidal agents, prostaglandins and steroids. The vagina also has great potential for systemic delivery because of its large surface area, rich blood supply and permeability to a wide range of compounds, including proteins and peptides. For example, the vagina offers a favorable alternative to the parenteral route for some drugs, including bromocriptine, propranolol, oxytocin, calcitonin, LHRH agonists, human growth hormone, insulin and steroids used in hormone replacement therapy or for contraception. In some embodiments, the film compositions of the present invention may be applied to a tampon or other delivery substrate before application to the vagina to achieve a desired pH.

In some other embodiments, the film may be applied to a wound in need of treatment. The film, or a bandage including the film composition, may be used to delivery a wound healing agent, including, without limitation, growth factors (e.g., Platelet-Derived Growth Factor), antimicrobial agents, wound cleansers, and moisturizers.

If desired, this film may be prepared and adhered to a second or support layer from which it is removed prior to use, i.e. application to the body surface. An adhesive may be used to attach the film to the support or backing material, which may be any of those known in the art, and is preferably not water soluble. If an adhesive is used, it will desirably be an adhesive that does not alter the properties of the active. Mucoadhesive compositions are also useful. The film compositions in many cases serve as mucoadhesives themselves.

The films of the present invention take advantage of the films' tendency to dissolve quickly when wetted. An active may be introduced to a liquid by preparing a film in accordance with the present invention, introducing it to a liquid, and allowing it to dissolve. This may be used to prepare a liquid dosage form of an active, which may then be topically applied.

A specific film shape or size may be preferred. Therefore, the film may be cut to any desired shape or size.

Figure 2:
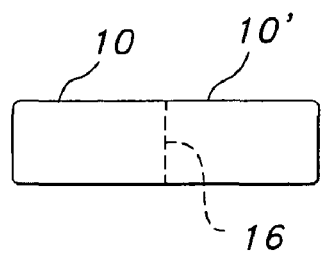
FIG. 2 shows a top view of two adjacently coupled packages containing individual unit dosage forms of the present invention, separated by a tearable perforation.
Figure 3:
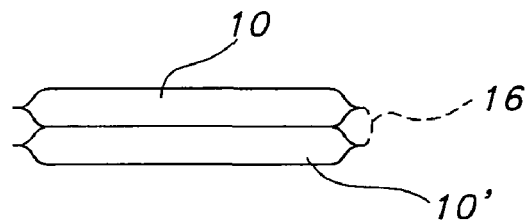
FIG. 3 shows a side view of the adjacently coupled packages of FIG. 2 arranged in a stacked configuration.
Figure 4:
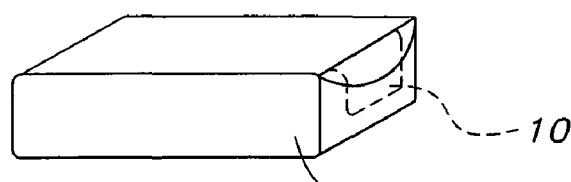
FIG. 4 shows a perspective view of a dispenser for dispensing the packaged unit dosage forms, dispenser containing the packaged unit dosage forms in a stacked configuration.
Figure 5:
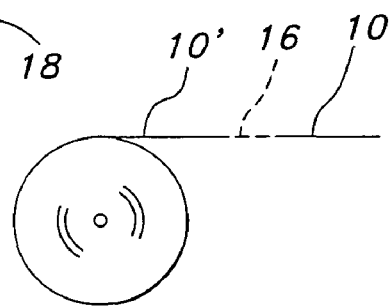
FIG. 5 is a schematic view of a roll of coupled unit dose packages of the present invention.

The films of the present invention are desirably packaged in sealed, air and moisture resistant packages to protect the topical active from exposure oxidation, hydrolysis, volatilization and interaction with the environment. Referring to FIG. 1, a packaged pharmaceutical dosage unit 10, such as a topical medicinal agent, is shown. Dosage unit 10 includes each film 12 individually wrapped in a pouch or between foil and/or plastic laminate sheets 14. As depicted in FIG. 2, the pouches 10, 10' can be linked together with tearable or perforated joints 16. The pouches 10, 10' may be packaged in a roll as depicted in FIG. 5 or stacked as shown in FIG. 3 and sold in a dispenser 18 as shown in FIG. 4. The dispenser may contain a full supply of the medication typically prescribed for the intended therapy, but due to the thinness of the film and package, is smaller and more convenient than traditional bottles used for tablets, capsules and liquids.

The films of the present invention may be designed to dissolve instantly or through a controlled, pulsed or sustained release profile, when placed in contact with a wetting agent, such as water or other solvent, or by contact with mucosal membrane areas. A wetting agent permits an active, which may be contained within the film, to be dissolved or dispersed out of the film. The active may then be easily applied to the skin or other particular surface area. In other embodiments, an active may be contained in a separate water soluble film in contact with the pH modulated film. Both films may include an active if desired. Upon contact of the water soluble films with a wetting agent or with a mucosal membrane area, the films dissolve thereby permitting the active or actives to be delivered to the site in need thereof under desired pH conditions.

Desirably, a series of such unit doses are packaged together in accordance with the prescribed regimen or treatment, e.g., a 10-90 day supply, depending on the particular therapy. The individual films can be packaged on a backing and peeled off for use.

The features and advantages of the present invention are more fully shown by the following examples which are provided for purposes of illustration, and are not to be construed as limiting the invention in any way.

EXAMPLES

Example 1

Incorporation of Citric Acid into a HPMC/PEO Film Base

The present example is directed to the incorporation of an acidic formulation into a hydroxypropylmethyl cellulose/PEO (80/20) film base. The film may be used alone or with another water soluble film if desired. The citric acid may be representative of an active ingredient that can be found in cosmetic or cleaning compositions. Alternatively, the citric acid may be used to modulate the pH of other components contained in the same film or a separate water soluble film. Citric acid is a chemically weak acid. In this example, the citric acid is combined with HPMC/PEO (neutral polymers) in the absence of a buffer system. Therefore, in the present example, the overall system is acidic. The resulting film was found to be useful as a dissolvable film for delivery of an acidic active (25% solids, by weight). The components are shown below in Table A.

TABLE A

| Components | Wt (g) |
| --- | --- |
| Polyethylene oxide WSR-N80 | 1.24 |
| Hydroxypropylmethyl cellulose E15 | 4.95 |
| Citric Acid | 6.25 |
| Sorbitan monooleate NF (Span 80)[1] | 0.06 |

[1]Available from Sigma-Aldrich Corp., St. Louis, MO.

The sorbitan monooleate from Table A and 37.5 g of distilled water were added to a Degussa 1100 bowl. Then, a blend of the polyethylene oxide and hydroxypropylmethyl cellulos (Table A) was added to the bowl. The combination of components was mixed using the Decussa Dental Multivac Compact. In particular, a solution was prepared by mixing the components at 125 rpm preset time intervals under increasing vacuum as set forth in Table B below, with the citric acid component being added right after the initial 40 minutes of mixing.

TABLE B

| Time (min) | Mixing Speed (rpm) | Vacuum (Hg) |
| --- | --- | --- |
| 20 | 125 | 17 |
| 20 | 125 | 24 |
| 12 | 125 | 26.5 |
| 8 | 125 | 28 |

The solution was cast into film using the K-Control Coater with the micrometer adjustable wedge bar set 410 microns onto the HDP side of 6330. HDP 6330 is a High Density Polyolefin coated paper. The film was dried 14 minutes in an 80° C. air oven to about 5.88% moisture (HR 73 Moisture Analyzer). The film released readily from the substrate.

The resulting film had a thickness of 3 mils, had moderate tear resistance, had sufficient strength when pulled, was not tacky, was not oily, and passed the 180° bend test out of the moisture analyzer. film had a film adhesion rating of 7 from the HDP of 6330.

A piece of the film dissolved readily when the film was tested using a dissolution test, which will now be described. Three 1×3 inch strips were cut, and the thickness and weight of each strip was noted, the strip was marked with a permanent marker at a location 1.5 inches up from the bottom of the strip. A weight, which weighed approximately 2.75 g, was attached to one end of the strip. A cushioned two jaw flask clamp was attached to the other end, such that the strip hung vertically from the clamp. The clamp, with the strip attached thereto, was then secured to a table top vertical support, which permitted the clamp to be unscrewed and the attached film strip raised or lowered into a beaker including water. The hanging strip was lowered quickly and without hesitation into 350 ml of 32-33° C. water to the 1.5 inch mark. Simultaneously, a stop watch was started as the piece was lowered to the mark. The watch was stopped as soon as the strip separated. The three strips were measured in this way, and averaged to obtain the dissolution time for a particular film composition.

In the present example, dissolution times of about 1.6 seconds were obtained. A 1×3 inch strip of the film weighed 104 mg. Two 1×3 inch strips of the film fit easily into the insertion tubes of tampons, along with the tampon. The film did not break or tear.

The present example demonstrates the feasibility of preparing a dissolvable film containing an acidic formulation using a neutral polymer system. It also demonstrates the feasibility of providing a tampon with a film coating of the present invention for delivery of an acidic composition to the vaginal area, where it may be useful in maintaining an acidic vaginal pH and/or providing some other therapeutic benefit.

Example 2

Incorporation of Citric Acid/Sodium Citrate into an HPMC/PEO Film Base

The present example is directed to the incorporation of both an acidic compound (citric acid) and a buffer system (sodium citrate) into a hydroxypropylmethyl cellulose/polyethylene oxide (80/20) film base. Approximately 50 mg citric acid and 50 mg of sodium citrate were incorporated into a 215 mg film strip, along with the neutral polymers, resulting in a neutral system (25 wt % solids). The components of the film are shown below in Table C.

TABLE C

| Components | Wt (g) |
| --- | --- |
| Polyethylene oxide WSR-N80 | 1.32 |
| Hydroxypropylmethyl cellulose | 5.30 |
| Sodium citrate | 2.91 |
| Citric acid | 2.91 |
| Sorbitan monooleate NF (Span 80) | 0.06 |

Sorbitan monooleate from Table C and 37.5 g of distilled water were added to a Degussa 1100 bowl. Then, a blend of the polyethylene oxide and hydroxypropylmethyl cellulose was added to the bowl. The combination of components was mixed using the Degussa Dental Multivac Compact under the conditions described in Table D below, with the citric acid being added after the initial 40 minutes of mixing, and the sodium citrate being added right after the 8 minute mixing interval.

TABLE D

| Time (min) | Mixing Speed (rpm) | Vacuum (Hg) |
| --- | --- | --- |
| 20 | 125 | 17 |
| 20 | 125 | 24 |
| 8 | 125 | 26.5 |

TABLE D-continued

| Time (min) | Mixing Speed (rpm) | Vacuum (Hg) |
|---|---|---|
| 4 | 125 | 26.5 |
| 4 | 125 | 28 |

The resulting solution had good viscosity before adding the sodium citrate. However, after adding the sodium citrate, the solution decreased in viscosity and showed gelling.

The present example demonstrates that acids and complementary bases, such as citric acid and sodium citrate at certain ratios, will cause a collapse of a neutral polymer system. This example further demonstrates the need for a modifier to prevent gelling in polymer system, where both an acid and a complementary base are present at certain ratios. Examples 3 and 4 below are directed to the use of an alginate polymer as a modifier in such neutral systems to prevent this type of gelling.

Example 3

Incorporation of Citric Acid and Sodium Citrate into a PEO/Propylene Glycol Alginate Film Base The present example is directed to the incorporation of citric acid, and its complementary base, sodium citrate into a polyethylene oxide/propylene glycol alginate (98/2) film base for use as a dissolvable film (34% solids, by weight). The film further included Tween 80. The components of the film are shown below in Table E. In some embodiments, the film may be used in conjunction with a second water soluble film.

TABLE E

| Components | Wt (g) |
|---|---|
| Polyethylene oxide WSR-N80 | 8.5 |
| Colloid 602[2] (propylene glycol alginate) | 0.17 |
| Citric Acid | 3.61 |
| Sodium citrate | 4.52 |
| Tween 80 NF spectrum | 0.36 |

[2]Available from TIC Gums, Belcamp, MD

The Tween 80 was combined with 33 g distilled water in a Degussa 1100 bowl. Then, a blend of the polyethylene oxide, citric acid and sodium citrate was added to the bowl. The combination of components was mixed using the Degussa Dental Multivac Compact under the conditions set forth in Table F below. The propylene glycol alginate (a modified basic polymer) was added as a modifier after the 8 minute mixing interval, when it was noticed that the solution had low viscosity and showed slight gelling (synerisis). After addition of the alginate polymer, and subsequent mixing for a 12 minute interval (at 17 Hg), the viscosity of the solution was desirable, and the synerisis (gelling) was gone.

TABLE F

| Time (min) | Mixing Speed (rpm) | Vacuum (Hg) |
|---|---|---|
| 8 | 150-200 | 17 |
| 12 | 125 | 17 |
| 20 | 125 | 24 |
| 12 | 125 | 26.5 |
| 4 | 125 | 28 |

The resulting solution was cast into film using the K-Control Coater with micrometer adjustable wedge bar set at 450 microns onto the HDP side of 6330. The film was dried 15 minutes in an 80° C. air oven to about 1.85% moisture (HR73 Moisture Analyzer).

The resulting film had a thickness of 3.8-4.5 mils, had good tear resistance, had adequate strength when pulled, was not tacky, and was not oily. The film had a good, smooth appearance when removed from the oven after drying. A 1 inch×3 inch piece of the film weighed 240 mg.

The present example demonstrated that acids and complementary bases, such as citric acid and sodium citrate at certain ratios, will cause collapse of a neutral polymer system, such as PEO. The present example also shows that the addition of small amounts of a basic polymer or a modified basic polymer, such as propylene glycol alginate, protects the polymer system and prevents synerisis. This is also shown below in Example 4, where the alginate polymer was added up front.

Example 4

Incorporation of Citric Acid and Sodium Citrate into a PEO/Propylene glycol Alginate Film Base (Alginate Polymer Added Up Front)

The present example is directed to the incorporation of citric acid and its complementary base, sodium citrate, into a polyethylene oxide/propylene glycol alginate (98/2) film base. In the present example, the alginate polymer was added up front as a polymer blend with the PEO. The resulting film was found to be useful as a dissolvable film strip (34% solids, by weight). The components of the film are shown below in Table G. The film may be used alone or with a second water soluble film.

TABLE G

| Components | Wt (g) |
|---|---|
| Polyethylene oxide WSR-N80 | 8.33 |
| Colloid 602 (propylene glycol alginate) | 0.17 |
| Citric acid | 4.05 |
| Sodium citrate | 4.05 |
| Tween 80 NF spectrum | 0.40 |

The Tween 80 component and 33 g of distilled water were placed in a Degussa 1100 bowl. Then, a blend of the polyethylene oxide and propylene glycol alginate was added to the bowl. A solution was prepared as described below in Table H using the Degussa Dental Multivac Compact, with the citric acid being added after the initial 20 minute mixing interval, and the sodium citrate being added after the 8 minute mixing interval.

TABLE H

| Time (min) | Mixing Speed (rpm) | Vacuum (Hg) |
|---|---|---|
| 20 | 125 | 17 |
| 8 | 125 | 24 |
| 12 | 150 | 24 |
| 12 | 100 | 26.5 |
| 8 | 100 | 28 |

The resulting solution was cast into film using the K-Control Coater with the micrometer adjustable wedge bar set at 355 microns onto the HDP side of 6330. The film was dried 15 minutes in an 80° C. air oven. The moisture content in the film was 2.89% (HR73=Moisture Analyzer).

The film had good tear strength, had adequate strength when pulled, was not sticky, was not oily, and had a film adhesion rating of 4 from the HDP side of 6330. A 1 inch×3 inch strip weighed 208 mg.

The present example demonstrates that addition of a basic polymer prevents collapse of a neutral polymer system that includes an acid and a complementary base at certain ratio.

Example 5

Incorporation of Citric Acid (50%) in a Sodium Alginate Film Base

In the present example, citric acid is incorporated at the 50% level into a sodium alginate film base (30 wt % solids, reduced to 27.5 wt % solids). This example shows that an acidic formulation, such as the citric acid, will not perform well in basic charged polymers, such as sodium alginate. In particular, it was found that the polymer recoils from the water phase in this instance, causing synerisis. The components of the film of the present example are shown below in Table I.

TABLE I

| Components | Wt (g) |
| --- | --- |
| Sodium alginate | 5.94 |
| Propylene glycol | 1.49 |
| Citric acid | 7.5 |
| Sorbitan monooleate NF (Span 80) | 0.075 |

Distilled water (35 g) was added to a Degussa 1100 bowl, along with the sodium alginate, propylene glycol, and sorbitan monooleate. A solution was prepared, as described below in Table J using the Degussa Dental Multivac Compact, with the citric acid being added after the 20 minute mixing interval at 24 Hg. After the 8 minute mixing interval at 26.5 Hg, it was noticed that some water loss occurred. Therefore, water was added back to the components to adjust for this loss, and an additional 4.55 g of distilled water was added, such that the wt % of solids was reduced to 27.5%.

TABLE J

| Time (min) | Mixing Speed (rpm) | Vacuum (Hg) |
| --- | --- | --- |
| 20 | 125 | 17 |
| 20 | 125 | 24 |
| 8 | 100 | 26.5 |
| 4 | 100 | 26.5 |
| 8 | 100 | 28 |

The resulting solution was cast into film using the K-Control Coater with the micrometer adjustable wedge bar set at 410 microns onto the HDP side of 6330. The film was dried for 13 minutes 80° C. air oven. The film had a moisture content of 4.61% (HR 73 Moisture Analyzer).

The film was not brittle. However, the solution was too viscous to coat well, and the polymer was recoiling from the water phase, causing synerisis. Therefore, this example demonstrates that acidic formulations do not work well in basic polymer systems, such as an alginate polymer.

Example 6

Incorporation of Sodium Bicarbonate into a HPMC/Polydextrose Film Base

The present example is directed to the incorporation of sodium bicarbonate at the 50 wt % level into a HPMC/polydextrose (60/40) film base (30 wt % solids). In some embodiments, sodium bicarbonate may be employed as an antacid in a film composition for oral use, for example. The present example demonstrates that a basic formulation, such as sodium bicarbonate, does not perform well in neutral polymer systems, such as the HPMC/polydextrose system. The components of the film composition of the present example are shown below in Table K.

TABLE K

| Components | Wt (g) |
| --- | --- |
| Hydroxypropyl methylcellulose (HPMC E15) | 4.46 |
| Polydextrose[3] | 2.97 |
| Sodium bicarbonate | 7.5 |
| Sorbitan monooleate NF (Span 80) | 0.075 |

[3]Stay-Lite III brand, available from Tate Lyle.

Distilled water (35 g) and the sorbitan monooleate were placed in a Degussa 1100 bowl. Then, a blend of HPMC and polydextrose was added to the bowl. A solution was prepared as described below in Table L, using a Degussa Dental Multivac Compact, with the sodium bicarbonate being added after the 12 minute mixing interval.

TABLE L

| Time (min) | Mixing Speed (rpm) | Vacuum (Hg) |
| --- | --- | --- |
| 20 | 125 | 17 |
| 20 | 100 | 24 |
| 12 | 100 | 26.5 |

The solution showed gelling (synerisis) after the sodium bicarbonate was added. Therefore, the solution was discarded. The present example shows that basic formulations will not work well in a neutral polymer system.

Example 7

Incorporation of Sodium Bicarbonate into a Sodium Alginate Film Base

The present example is directed to incorporation of sodium bicarbonate at the 50% level into a sodium alginate film base (30% solids, by weight). The components of the film are shown below in Table M. The film may be used alone or in conjunction with a second water soluble film.

TABLE M

| Components | Wt (g) |
| --- | --- |
| Sodium Alginate | 6.68 |
| Propylene glycol | 0.74 |
| Sodium bicarbonate | 7.5 |
| Sorbitan monooleate NF (Span 80) | 0.075 |

Distilled water (35 g, preheated to 82° C.) was added to a Degussa 1100 bowl, along with the sodium alginate, propylene glycol, and sorbitan monooleate. A solution was prepared as described in Table N using the Degussa Dental Multivac Compact, with the sodium bicarbonate being after the 12 minute mixing interval.

TABLE N

| Time (min) | Mixing Speed (rpm) | Vacuum (Hg) |
| --- | --- | --- |
| 4 | 200 | 17 |
| 16 | 125 | 17 |
| 20 | 100 | 24 |
| 12 | 100 | 26.5 |
| 8 | 100 | 28 |

The resulting solution did not show gelling (i.e., no syneri-sis) and was cast into film using the K-Control Coater with the micrometer adjustable wedge bar set at 460 microns onto the HDP side of 6330. The film was dried for 15 minutes in an 80° C. air oven. The percent moisture of the film was 2.6% (HR73 Moisture Analyzer).

The present example demonstrates that a basic formulation, such as sodium bicarbonate, works well in a basic polymer system like alginate, and does not show synerisis.

What is claimed is:

1. A composition comprising:
   (a) at least one component having a non-neutral pH when combined with water; and
   (b) a pH modulated polymer system selected to reduce or prevent synerisis when combined with said non-neutral component in combination with water, wherein said pH modulated polymer system comprises a neutral polymer and propylene glycol alginate, wherein said neutral polymer is a combination of hydroxypropyl methylcellulose and polyethylene oxide.

2. The composition of claim 1, wherein the composition is in the form of a film.

3. The composition of claim 2, wherein the film includes an active.

4. The composition of claim 3, wherein the active is the non-neutral component.

5. The composition of claim 3, wherein the active is a different component from the non-neutral component.

6. The composition of claim 1, wherein said at least one non-neutral component is acidic, and said polymer system comprises a neutral or acidic polymer.

7. The composition of claim 1, wherein said at least one non-neutral component is acidic, and said polymer system comprises a neutral polymer, a basic polymer and a weak base.

8. The composition of claim 1, wherein said at least one non-neutral component is basic, and said polymer system comprises a neutral polymer, a basic polymer and a weak acid.

9. The composition of claim 1, wherein said at least one non-neutral component is basic, and said polymer system comprises at least one basic polymer.

10. The composition of claim 1, wherein said polymer system provides a neutral pH when combined with said non-neutral component in combination with water.

11. The composition of claim 1, wherein said polymer system comprises a buffer system.

12. The composition of claim 11, wherein said buffer system comprises a weak acid, a weak base, or salts thereof 13. The composition of claim 12, wherein said weak acid is selected from the group consisting of acetic acid, ascorbic acid, benzoic acid, butyric acid, carbonic acid, citric acid, formic acid, lactic acid, malic acid, nitrous acid, oxalic acid, phosphoric acid, propanoic acid, propionic acid, pyrophosphoric acid, pyruvic acid, valeric acid and combinations thereof.

14. The composition of claim 12, wherein said buffer system comprises a salt of an organic acid.

15. The composition of claim 14, wherein said organic acid salt is citrate.

16. The composition of claim 1, wherein said pH modulated system comprises 98% of said neutral polymer.

17. A composition comprising:
   (a) at least one component having a non-neutral pH when combined with water; and
   (b) a pH modulated polymer system selected to reduce or prevent synerisis when combined with said non-neutral component in combination with water, wherein said pH modulated polymer system comprises a neutral polymer and propylene glycol alginate, wherein said neutral polymer is polyethylene oxide.

18. The composition of claim 17, wherein the composition is in the form of a film.

19. The composition of claim 18, wherein the film includes an active.

20. The composition of claim 19, wherein the active is the non-neutral component.

21. The composition of claim 19, wherein the active is a different component from the non-neutral component.

22. The composition of claim 17, wherein said at least one non-neutral component is acidic, and said polymer system comprises a neutral or acidic polymer.

23. The composition of claim 17, wherein said at least one non-neutral component is acidic, and said polymer system comprises a neutral polymer, a basic polymer and a weak base.

24. The composition of claim 17, wherein said at least one non-neutral component is basic, and said polymer system comprises a neutral polymer, a basic polymer and a weak acid.

25. The composition of claim 17, wherein said at least one non-neutral component is basic, and said polymer system comprises at least one basic polymer.

26. The composition of claim 17, wherein said polymer system provides a neutral pH when combined with said non-neutral component in combination with water.

27. The composition of claim 17, wherein said polymer system comprises a buffer system.

28. The composition of claim 27, wherein said buffer system comprises a weak acid, a weak base, or salts thereof.

29. The composition of claim 28, wherein said weak acid is selected from the group consisting of acetic acid, ascorbic acid, benzoic acid, butyric acid, carbonic acid, citric acid, formic acid, lactic acid, malic acid, nitrous acid, oxalic acid, phosphoric acid, propanoic acid, propionic acid, pyrophosphoric acid, pyruvic acid, valeric acid and combinations thereof.

30. The composition of claim 27, wherein said buffer system comprises a salt of an organic acid.

31. The composition of claim 30, wherein said organic acid salt is citrate.

32. A composition comprising:
   (a) a component having an acidic pH when combined with water; and
   (b) a polymer system comprising at least one neutral or acidic polymer and propylene glycol alginate, wherein said neutral polymer is polyethylene oxide.

33. The composition of claim 32, wherein the composition is in the form of a film.

34. The composition of claim 33, wherein the film includes an active.

35. The composition of claim 34, wherein the active is the acidic component.

36. The composition of claim 34, wherein the active is a different component from the acidic component.

37. The composition of claim 32, wherein said a polymer system comprises 98% of said at least one neutral or acidic polymer.

38. A device comprising:
   (a) a film composition comprising
      (i) at least one component having a non-neutral pH when combined with water; and
      (ii) a pH modulated polymer system selected to reduce or prevent synerisis when combined with said non-neutral component in combination with water, wherein said pH modulated polymer system comprises a neutral polymer and propylene glycol alginate; and (b) a delivery substrate, wherein said delivery substrate is a bandage.

39. The composition of claim 38, wherein the film composition includes an active.

40. The composition of claim 39, wherein the active is the non-neutral component.

41. The composition of claim 39, wherein the active is a different component from the non-neutral component.

42. The device of claim 38, wherein said pH modulated system comprises 98% of said neutral polymer.

* * * * *